United States Patent [19]
Elrod et al.

[11] Patent Number: 5,934,904
[45] Date of Patent: Aug. 10, 1999

[54] DENTAL INSTRUMENT AND PROCESSES

[75] Inventors: DeLynn Roy Elrod; Joseph Mark Forehand; Vernon Kim Kutsch, all of Albany, Oreg.; Bryan G. Moore, Carlsbad, Calif.

[73] Assignee: Kreativ, Inc., San Diego, Calif.

[21] Appl. No.: 08/975,438

[22] Filed: Nov. 21, 1997

Related U.S. Application Data

[60] Provisional application No. 60/062,406, Oct. 14, 1997.

[51] Int. Cl.$^6$ .................................................. A61C 3/02
[52] U.S. Cl. .................................. 433/88; 433/27; 433/84
[58] Field of Search ................................ 433/88, 101, 98, 433/80, 84, 27; 451/75, 78; 601/162

[56] References Cited

U.S. PATENT DOCUMENTS

| | | | |
|---|---|---|---|
| 3,487,828 | 1/1970 | Troy | 601/162 |
| 3,989,952 | 11/1976 | Hohmann | 433/101 |
| 4,114,275 | 9/1978 | Jones et al. | 433/101 |
| 4,446,456 | 5/1984 | Beier | 433/101 |
| 4,635,897 | 1/1987 | Gallant | 251/5 |
| 4,676,750 | 6/1987 | Mason | 433/101 |
| 4,708,534 | 11/1987 | Gallant | 406/75 |
| 4,733,503 | 3/1988 | Gallant et al. | 51/410 |
| 4,818,227 | 4/1989 | Krueger | 433/27 |
| 4,893,440 | 1/1990 | Gallant et al. | 51/436 |
| 5,334,016 | 8/1994 | Goldsmith et al. | 433/88 |
| 5,618,177 | 4/1997 | Abbott | 433/88 |
| 5,636,983 | 6/1997 | Shoji et al. | 433/88 |
| 5,752,829 | 5/1998 | Goldsmith et al. | 433/88 |

FOREIGN PATENT DOCUMENTS

| | | | |
|---|---|---|---|
| 3243294 | 5/1984 | Germany | 433/101 |
| 3413277 | 10/1985 | Germany | 433/101 |

OTHER PUBLICATIONS

Rosenberg, Stewart; Air Abrasion: The New Standard of Care; Dentistry Today, Jul. 1996.
Kehoe, Bob; Assessing Air Abrasion; Dental Practice & Finance; Mar./Apr. 1997.
Reality Now; The Ratings: Air Abrasion Units, Updated Commentary, Oct. 1996.
Rosenberg, Stewart; Air–Abrasive Microdentistry—A New Standard of Care; Focus.
Kreativ, Inc.; Mach 4.0 Air Abrasion Operator's Manual, Service Manual, Site Preparation Guide.
Kreativ, Inc.; Mach 4.1 Advertising Flyer, Sep. 1996.
Rosenberg,S: DDRT; Air Abrasion Takes Off, 1997.

*Primary Examiner*—John J. Wilson
*Assistant Examiner*—Patrick A. Hilsmier
*Attorney, Agent, or Firm*—Lori M. Friedman

[57] ABSTRACT

A dental instrument includes a handpiece having a nozzle from which is ejected a stream of abrasive particles, and valves operated under the control of a microprocessor which regulate, as selected by a user, the stream of abrasive particles either as a continuous flowing stream or a pulsed flowing stream. The microprocessor enables the valves to be operated at a plurality of different pulse durations. A remote control unit, small enough to fit into the palm of a hand of a user, provides control of the basic parameters of the instrument, allowing the instrument to be conveniently placed and allowing fingertip control of the instrument without having to move away from the patient. The handpiece is integrated with a main dental unit foot control for a dental drill, so that the main dental unit foot control operates both the dental drill and the handpiece.

48 Claims, 11 Drawing Sheets

SECTION A—A

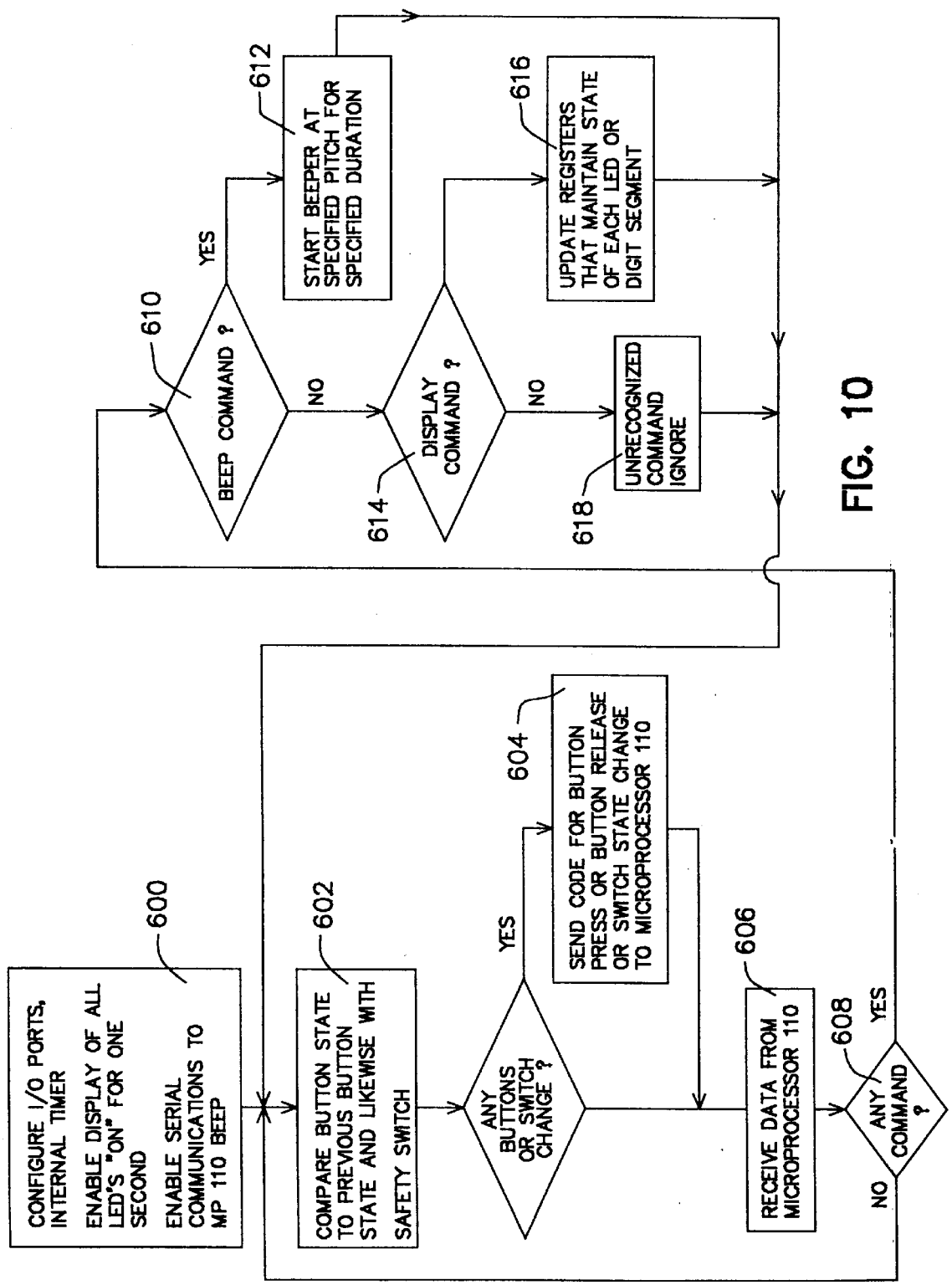

DENTAL INSTRUMENT AND PROCESSES

RELATED PATENT APPLICATIONS

This is a utility patent application based on a United States provisional patent application Ser. No. 60/062406, filed, Oct. 14, 1997, and entitled "Air Abrasion Dental Instrument."

BACKGROUND OF THE INVENTION

Field of the Invention

The present invention is directed to a microprocessor-controlled dental instrument. More specifically, this instrument may be used in various dental treatments including removing areas of decay from a tooth structure, preparing a tooth for resurfacing, cleaning teeth, and the like.

Background of the Invention

The use of air abrasion in dentistry has been known for several years. Rosenberg, in the July, 1996 issue of Dentistry Today refers to air abrasion as the new standard in dental care. This article enumerates many advantages realized in air abrasion including increased patient comfort, alleviation of patient anxiety, decreased use of anesthesia, increase of dentists' productivity, and decreased costs to both patients and dentists.

Air abrasion instruments have been available for use by dentists for treating patients with an abrasive-laden fluid for many years. Such fluids include abrasive-laden air directed onto the patient's teeth for removal of decay, preparing the teeth to receive fillings, prophylactic treatment, and so on. Such abrasion instruments provide advantages over conventional dental drills. These include eliminating the heat, noise, and vibration produced by conventional high-speed drills. Also eliminated in many cases is the need for anesthesia as well as the need to cool the drill with fluid.

There are, however, issues of concern involved with the use of air abrasion. One of the desired improvements in this technology is to cut efficiently at moderate or low air pressures, while avoiding the use of potentially dangerous high pressure. Higher pressure (ranging from about 100–160 psi) increases the cutting speed of the air abrasion dental instrument, but this pressure level can be injurious for the patient causing such injury as air emphysema. Rosenberg, in the reference above, suggests using the lowest air pressure possible. Reasons cited include patient comfort and better control and visibility for the dentist.

Another disadvantage of using high pressures is that as the abrasive air fluid exhausts from the air abrasion instrument, an immediate drop in pressure occurs. This pressure drop causes the fluid to decrease in temperature. The static temperature of the fluid can decrease to, for instance, about 20 degrees Fahrenheit. At this temperature, air flow against a patient's tooth can cause extreme discomfort. In order to compensate for this, a heater may be needed. Another alternative to compensate for the coldness of the air stream would be to employ anesthetic, requiring the use of a hypodermic needle. Patient discomfort, the need for anesthetics, and the use of needles are contrary to the use of air abrasion dentistry. Since the lessening of patient anxiety and discomfort are basic tenets of air abrasion, these remedies for high pressure use are not acceptable.

In the past, various methods of feeding particulate abrasive have been attempted. Gallant in U.S. Pat. No. 4,708,534 discusses the use of particulate abrasive material in a pressurized gas stream. The stream is used to perform various procedures under uniform pressure.

The use of high pressure in abrasive jet machining is mentioned in U. S. Pat. No. 4,733,503 and U.S. Pat. No. 4,893,440 to Gallant et al. Disclosed herein is the use of high pressure using abrasive-laden gas streams. Pressures of several hundred psi up to 2,000 psi are disclosed.

U.S. Pat. No. 4,635,897 relates to a tube flow shut-off device. This shut-off device is for a tube formed of flexible material and adapted to carry a fluid. Control of fluid flow of the instant invention is microprocessor controlled. The entire operation of the unit of this invention is regulated by the microprocessor. U.S. Pat. No. 5,618,177 to Abbott discloses an arrangement for feeding pressurized particulate material which overcomes several drawbacks of earlier air abrasion equipment. Microprocessor control is not one of the suggested improvements.

These prior examples of pressure use in air abrasion dentistry neither mention nor suggest the use of microprocessor-controlled pulsed mechanism for improved cutting efficiency and control of the instrument. Neither do they mention or suggest other methods of increasing particle speed besides the use of high pressure.

In an article in the March/April 1997 issue of Dental Practice & Finance, Bob Kehoe authored an article entitled "Assessing Air Abrasion". This article, which is intended to provide advice on the use of air abrasion dentistry, states that air abrasion is "designed to conservatively cut virgin teeth, remove sealants and composite restoration, not amalgam or other metals." In light of this recent assessment, the results of the applicant in removing amalgam with air abrasion techniques and the unit of the instant invention is a significant improvement.

Another publication doubting the possibility of amalgam removal with air abrasion appears in Reality NOW in the October, 1996 issue. In its ratings and updated commentary on air abrasion units, it lists amalgam removal as a contraindication for the use of air abrasive. Again, the results of the applicants in removing amalgam with air abrasion techniques and the unit of the instant invention is quite surprising and remarkable.

In another dental industry publication, DDRT (Dentists' Desktop Reference to Technology), Rosenberg mentions amalgam removal using air abrasion. He states that a supersonic nozzle employed in the instrument Mach 4.0 manufactured by Kreativ, Inc., the assignee of this invention, is key to successful amalgam removal using air abrasion. This article not does mention the unique features of the air abrasion unit of this invention, such as pulsing and microprocessor control thereof, and their importance to successful amalgam removal.

SUMMARY OF THE INVENTION

This invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENTS," one will understand how the features of this invention provide its benefits, which include improved patient care in that less time is required to conduct procedures, in many cases without anesthetic, and increased versatility in controlling parameters of the particle laden stream during treatment of a patient.

The first feature of the dental instrument of this invention is that it includes a handpiece having a nozzle from which is ejected a stream of abrasive particles, and a control valve operated under the control of a main central microprocessor which regulates, as selected by a user, the stream of abrasive particles either as a continuous flowing stream or a pulsed flowing stream. The pulsed stream is produced by an air supply system having an on-off valve which is opened and closed rapidly to bring the stream to a selected pressure. The nozzle, which may be a supersonic nozzle, is held in an assembly at an angle ranging from 45° to 90°, and has a diameter ranging between 0.01 and 0.03 inch. Preferably, the handpiece is integrated with a main dental unit foot control for a dental drill, so that the main dental unit foot control selectively operates both the dental drill and the handpiece. A collection canister may be provided into which abrasive particles in the handpiece are collected when the flow of the stream is discontinued. Preferably, the handpiece is operated under the control of a foot control pedal which is depressed by the user to turn on the flow of the stream.

The second feature is that the microprocessor enables the control valve to be operated at a plurality of different pulse durations. To facilitate amalgam removal, the handpiece has a supersonic nozzle, and the pulse duration, as adjusted by the microprocessor, has an ON time ranging from 190 to 250 milliseconds and an OFF time ranging from 80 to 140 milliseconds. To facilitate precision control for cavity preparation, the pulse duration, as adjusted by the microprocessor, has an ON time ranging from 235 to 295 milliseconds and an OFF time ranging from 30 to 80 milliseconds. To facilitate cleaning, stain removal, and small lesion treatment, the continuous mode is selected. The stream pressure in the continuous mode for this application ranges from 15 to 120 psi, and the abrasive particle flow rate is from 2 to 3 grams per minute. The microprocessor preferably is programmed to provide a self-diagnostic routine and to hold the instrument at standby until a user manually actuates the instrument.

The third feature is a remote control unit which signals the main central microprocessor to provide control of parameters for the stream. This remote control unit includes another microprocessor which is coupled to the main central microprocessor. Preferably, the remote control unit is small enough to fit into the palm of a hand of the user. The use of the remote control unit allows the larger and bulky components of the instrument to be housed in a central unit remotely located from the patient. Nevertheless, the remote control unit provides fingertip control of the instrument without having to move away from the patient. When not in use, the handpiece is seated in a cradle on the remote control unit having a safety switch which is engaged by the handpiece when seated in the cradle to enable the microprocessor to recognize when the user is holding the handpiece. The remote control unit includes a warning system having indicators which, in response to the self-diagnostic routine, alert the user that one or more of the following defective conditions prevail: a valve is defective, that the instrument needs service, that the collection canister needs to be emptied, that an adequate supply level of abrasive powder is not available, and that an operating system error exists. The operating system error may be inadequate available pressure, leaking fluid supply lines, or the inability to reach or sustain desired voltages for the instrument's operation. A non-volatile read/ write memory connected to the microprocessor retains the last selected values of predetermined parameters of the stream of abrasive particles as manually selected by the user through the remote control unit. The remote control unit optionally includes an audio alarm which is activated when one or more of the following conditions prevail: an air pressure selected by the user exceeds the limits of the instrument, an abrasive loading selected by the user exceeds the limits of the instrument, the safety switch for the handpiece for the instrument indicates that the handpiece has not been lifted from the cradle for the handpiece.

The instrument is a combination of some of the these and other features. In one combination of features, first and second valves are used. The first valve has an open position and a closed position, and in the open position it permits gas to flow into a mixing chamber and in the closed position prevents gas from flowing into the mixing chamber. This enables gas pressure within the mixing chamber to be increased incrementally. The second valve is between the mixing chamber and the handpiece. This second valve is operated at a first operational mode that provides the pulsed stream of particle laden gas or at a second operational mode that provides the continuous stream of particle laden gas. A pressure sensor detects the pressure of the gas within the mixing chamber and provides a control signal indicating the pressure detected. The remote control unit enables the user to select (a) the pressure of the gas within the mixing chamber and (b) the operational mode. The microprocessor controls the operation of the first valve to turn this first valve on and off until the gas pressure of the stream corresponds to the gas pressure selected by the user actuating the remote control unit. The remote control unit also enables the user to select the concentration of particles in the gas steam. The pressure of the mixing chamber is increased incrementally by selectively opening and closing the first valve. The first operational mode is achieved by selectively opening and closing the second valve to create the pulsed stream and the second operational mode is achieved by maintaining the second valve continuously open to create the continuous stream. The pulsed stream of the first operational mode is at different pulse durations as selected by a user.

In a second combination of features, a sensor detects the pressure of the stream of abrasive particles, and an air supply system employs the on-off valve which is opened and closed rapidly to bring the stream of abrasive particles to a selected pressure. The microprocessor controls the operation of the on-off valve in response to the pressure detected by the sensor to regulate the pressure of the stream of abrasive particles. The remote control unit, operated manually by the user, signals the microprocessor to set the pressure of the stream of abrasive particles to a pressure selected by the user.

In one embodiment of the invention, a system is provided which delivers to a plurality of different operatories, under the control of a user in each individual operatory, separate streams of abrasive particles provided by a remote mixing chamber in which abrasive particles are mixed with gas. This mixing chamber is part of a central unit which also contains the main central microprocessor. Each individual operatory includes a handpiece from which is ejected a stream of abrasive particles. Each handpiece has a first operational mode that provides a pulsed stream of particle laden gas and a second operational mode that provides a continuous stream of particle laden gas. In each operatory is a remote control unit which each user uses to signal the main central microprocessor to provide control of the parameters for the stream being ejected from each handpiece in each operatory. The remote control unit in each operatory is under the common but separate control of the main central microprocessor which allows each user at each individual operatory to select the operational mode of the handpiece at such individual operatory.

This invention also includes a dental process wherein a pulsed stream of abrasive particles is directed at a tooth structure. The pulsed stream is created by opening and closing a valve operated by a microprocessor which responds to command signals from a remote control unit including a selector control which enables a user to select wether the stream should be a pulsed or continuous stream. Pulse duration may also be selected. The abrasive particles are at a relatively high particle speed ranging from 110 to 160 meters per second and at an abrasive particle flow rate ranging from 1 to 10 grams per minute. The stream is at a pressure ranging from 15 to 120 psi. To remove amalgam from the tooth structure, the stream is directed at the tooth structure through a supersonic nozzle, with the stream being in the form of pulses and the pressure of the stream exceeding 40 psi and the abrasive particle flow rate ranging from 1 to 10 grams per minute. To prepare a tooth structure for veneer restoration, facing restoration, pit and fissure sealants, partial or complete removal of composite restorations, or repair of restoration failure sites, the stream is directed as a pulsed stream at the tooth structure at a pressure of from 40 to 80 psi and the abrasive particle flow rate is up to 5 grams per minute. A supersonic nozzle may be used. To prepare a tooth structure for etching metal, porcelain, or composite restorations prior to repair, the stream is directed at the tooth structure as a continuous, non-pulsed stream at a pressure of less than about 80 psi, preferably about 60–80 psi, and the abrasive particle flow rate is up to 5 grams per minute. To clean a tooth structure, the stream is directed at the tooth structure as a continuous, non-pulsed stream at a pressure of from 20 to 40 psi and the abrasive particle flow rate ranges from about 2 to 3 grams per minute. The abrasive particles are selected from the group consisting of aluminum oxide, dolomite, and sodium bicarbonate, and they are at a relatively high particle speed ranging from 110 to 160 meters per second and at an abrasive particle flow rate ranging from 1 to 10 grams per minute. The stream is preferably at a pressure ranging from 15 to 120 psi. The diameter of the nozzle may be selected for particular dental procedures including a 0.018 inch diameter nozzle to remove large lesions and existing restorations, a 0.014 inch diameter nozzle for most small lesions, a 0.011 inch diameter nozzle for very precise cutting, diagnosis of occlusal pits and fissures, incipient Class II and III lesions or for placing fine retention in Class IV and V restorations.

DESCRIPTION OF THE DRAWING

The preferred embodiments of this invention, illustrating all its features, will now be discussed in detail. These embodiments depict the novel and non-obvious dental instrument and process of this invention as shown in the accompanying drawing, which is for illustrative purposes only. This drawing includes the following figures (FIGS.), with like numerals indicating like parts:

FIG. 10 is logic flow diagram depicting the main routines of the program for the remote microprocessor housed in the remote control unit.

DETAILED DESCRIPTION OF PREFERRED EMBODIMENTS OF THE INVENTION

Figure 8:
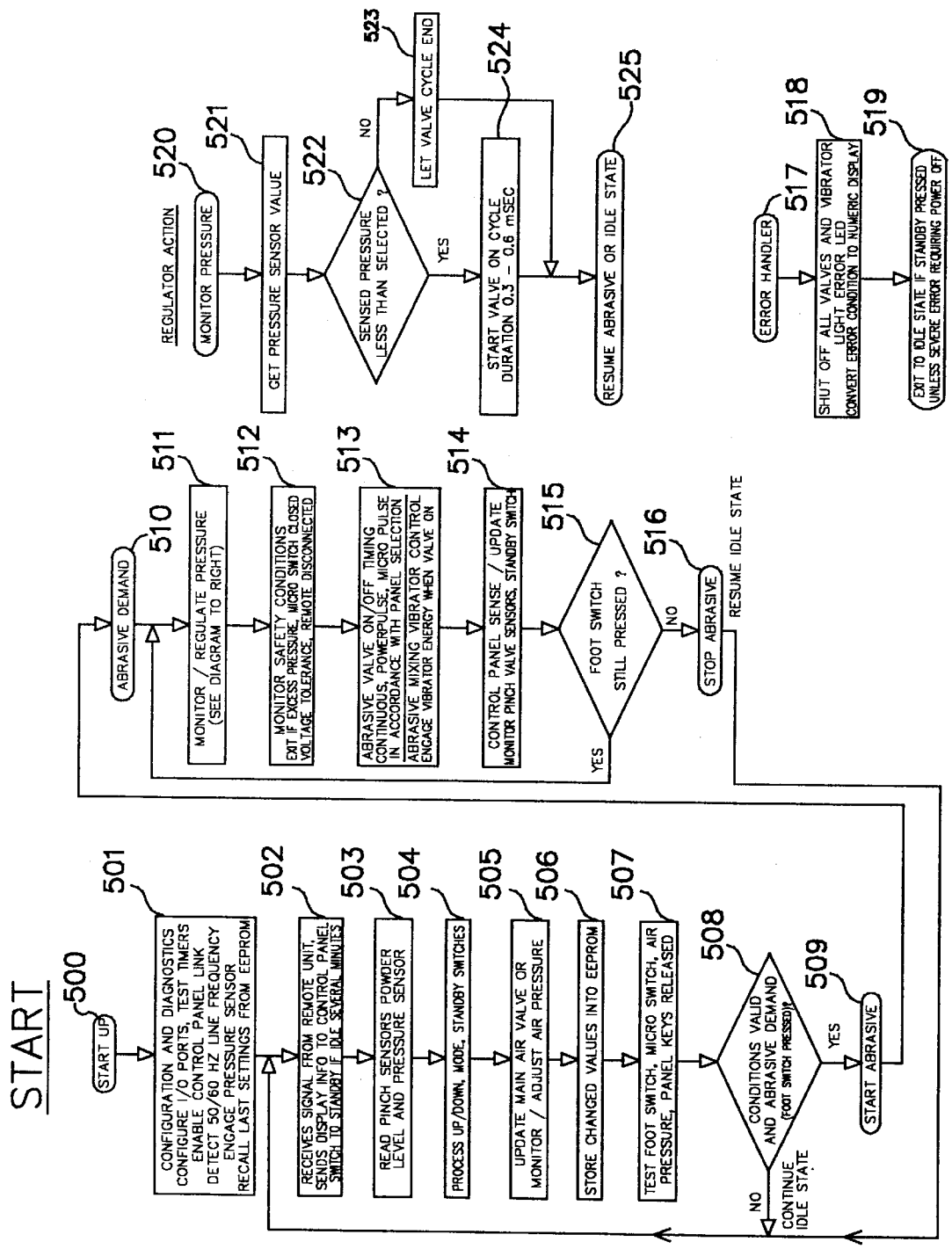
FIG. 8 is a logic flow diagram depicting the main routines of the program for the main central microprocessor used to control the operation of the instrument of the present invention.
Figure 8A:
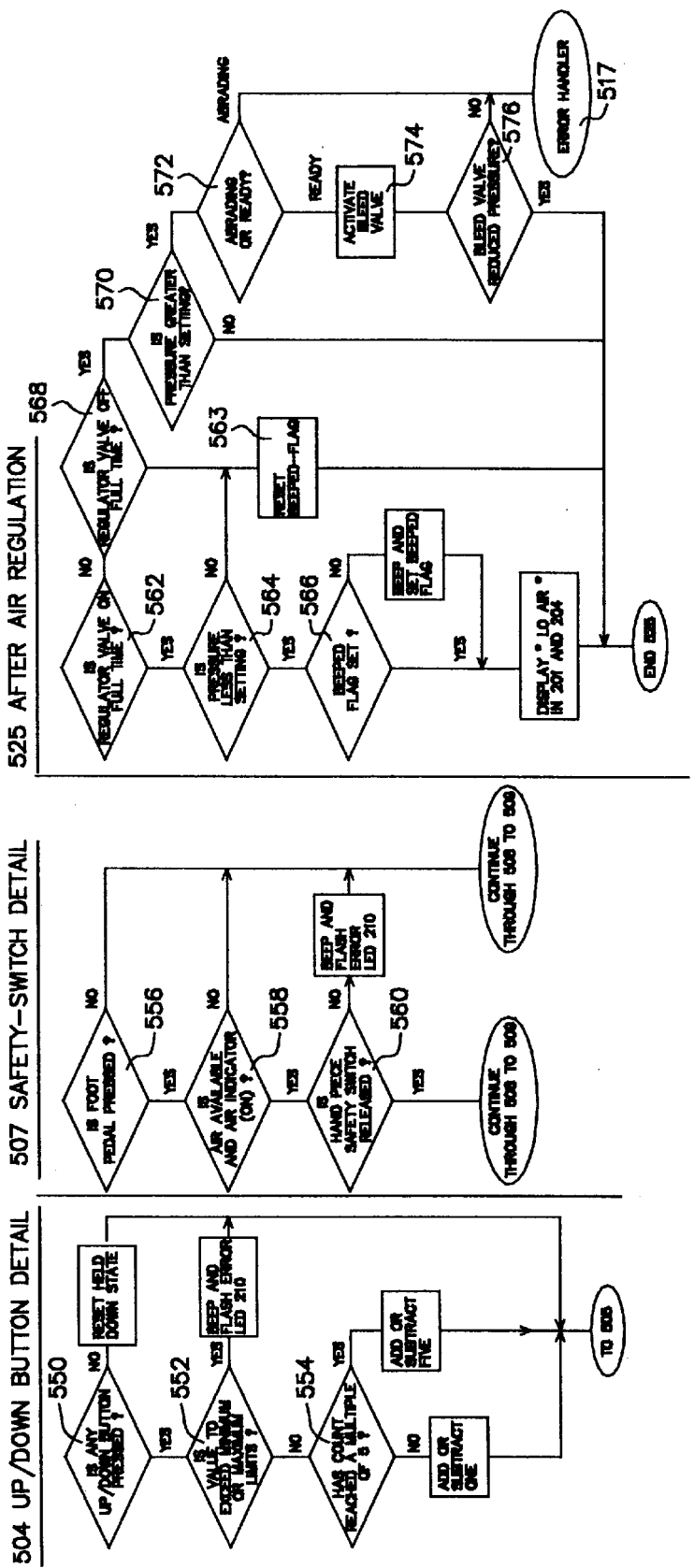
FIG. 8A is a logic flow diagram depicting the sub-routines routines of the program for the main central microprocessor for controlling the audio alarm of the present invention.

As schematically illustrated in FIGS. 1 through 6, the major components of the dental instrument 1 of this invention include an air pressure regulator 100, an abrasive mixing chamber 102, a main central microprocessor 110, a handpiece 116, which sits in a cradle 115 of a remote control unit 118. The remote control unit 118 includes a remote microprocessor 123 for controlling the internal operations of this unit. Both these microprocessors 110 and 123 are programmed in accordance with conventional techniques and the flow diagram of the program for the main central microprocessor 110 is shown in FIGS. 8 and 8A and the flow diagram of the program for remote control unit 118 is shown in FIG. 10. Both these programs are discussed subsequently in greater detail.

Using the remote control unit 118, a dentist adjusts the parameters of an abrasive particle laden stream being ejected from a nozzle 116a of the handpiece 116. Specifically, the pressure of this stream at which the dentist desires to conduct the treatment of a tooth structure may be either increased or decreased, the loading of abrasive particles in the stream may be either increased or decreased, the stream may be either a continuous or pulsed stream, and the duration of the pulses in the pulsed stream may be either increased or decreased. The particle laden stream, either continuous or pulsed, removes from the tooth being treated undesirable dental material. This stream performs cutting, abrading, deburring, peening, and polishing of tooth structures. There is minimal disturbance of healthy enamel or healthy dentin during removal of these undesirable materials.

The pressure of the particle laden stream may be varied over a wide range of pressure values ranging from a high pressure corresponding to a maximum inlet line pressure not to exceed about 120 psi (pounds per square inch) to a low pressure of about 20 psi. The dentist may incrementally vary pressure one psi at a time within this range. The pulsed particle laden stream is at one of two different pulsed conditions, namely, a Power Pulse™ mode or a Micro Pulse™ mode. In the Continuous mode, a non-pulsed, continuous particle laden stream exits the nozzle 116a of the handpiece 116. In the pulsed mode, a pulsed particle laden stream exits the nozzle end of the handpiece. The duration of the pulse is longer in the Power Pulse™ setting, typically having an ON time ranging from 235 to 295 milliseconds and an OFF time ranging from 30 to 80 milliseconds than in the Micro Pulse™ setting, typically having an ON time ranging from 190 to 250 milliseconds and an OFF time ranging from 80 to 140 milliseconds. If, for example, the dentist selects a pressure or particle loading which exceeds the limits of the instrument 1, an audio alarm, for example a beeper 118a, is activated.

Air under pressure from an air source, typically at about 80 psi (although higher or lower pressure air may be used, with a maximum of about 120 psi), is introduced through a master valve 64 and tube 64a into an inlet 100a of an air pressure regulator 100, including an "on/off" valve 99. The air source is usually a compressor in the dentist's office or, in the case of an alternate embodiment of the dental instrument 1, the compressor is a component of the instrument itself. The "on/off" valve 99 in the regulator 100 is operated by a solenoid 18 energized under the control of the main central microprocessor 110 which transmits a control signal over a line 20 to the solenoid. There is a sensor 10a in the tube 64a between the master valve 64 and the inlet 100a of the regulator 100 which provides a control signal to the central microprocessor 110 when the inlet pressure is inadequate (typically less than about 20 psi) to operated the instrument 1. An outlet 100b of the air pressure regulator 100 is connected through a tube 120 to a pressure sensor 10 which detects the internal pressure of the dental instrument 1 and provides a control signal via a line 12 to the central microprocessor 110. The outlet 100b of the air pressure regulator 100 is also connected through a tube 101 to a mixing chamber 102 of an abrasive delivery system 50 shown in FIGS. 3, 3A, and 3B through a branched tube 106 to a dump pinch valve 104-C of a pulse control module 104. In the mixing chamber 102 abrasive powder P (FIG. 3) is mixed with the pressurized air from the regulator 100.

The pulse control module 104 regulates the pulse duration when the dental instrument 1 is in the pulsed mode and discontinues pulsing when in the continuous mode. It includes, in addition to the dump pinch valve 104-C, an abrasive pinch valve 104-A and a bleed pinch valve 104-B. Under the control of the central microprocessor 110, via an electromagnetic pneumatic control module 112, the pinch valves 104A, 104B, and 104C are opened and closed. Each of these valves 104A, 104B, and 104C has a piston-type mechanism (not shown) which, in the closed position, pinches to close the tube it engages. To open any one of these pinch valves 104A, 104B, and 104C, the piston-type mechanism is exposed to atmospheric pressure (14.7 psi) and to close any one of these pinch valves, the piston-type mechanism is exposed to the internal pressure of the dental instrument 1, which exceeds 20 psi when the dental instrument has been switched to "on" by depressing a button 208 on the remote control unit 118. As the pinch valve 104A is opened and closed rapidly it creates a pulsed stream. Or, the pinch valve 104A may simply be set in an open condition to create the continuous stream. The pressure of each individual pulse typically ranges from about 20 to 120 psi. The central microprocessor 110 controls the pressure of the air stream in response to both (a) the control signal from the sensor 10 and (b) a control signal provided by the remote control unit 118.

Figure 2:
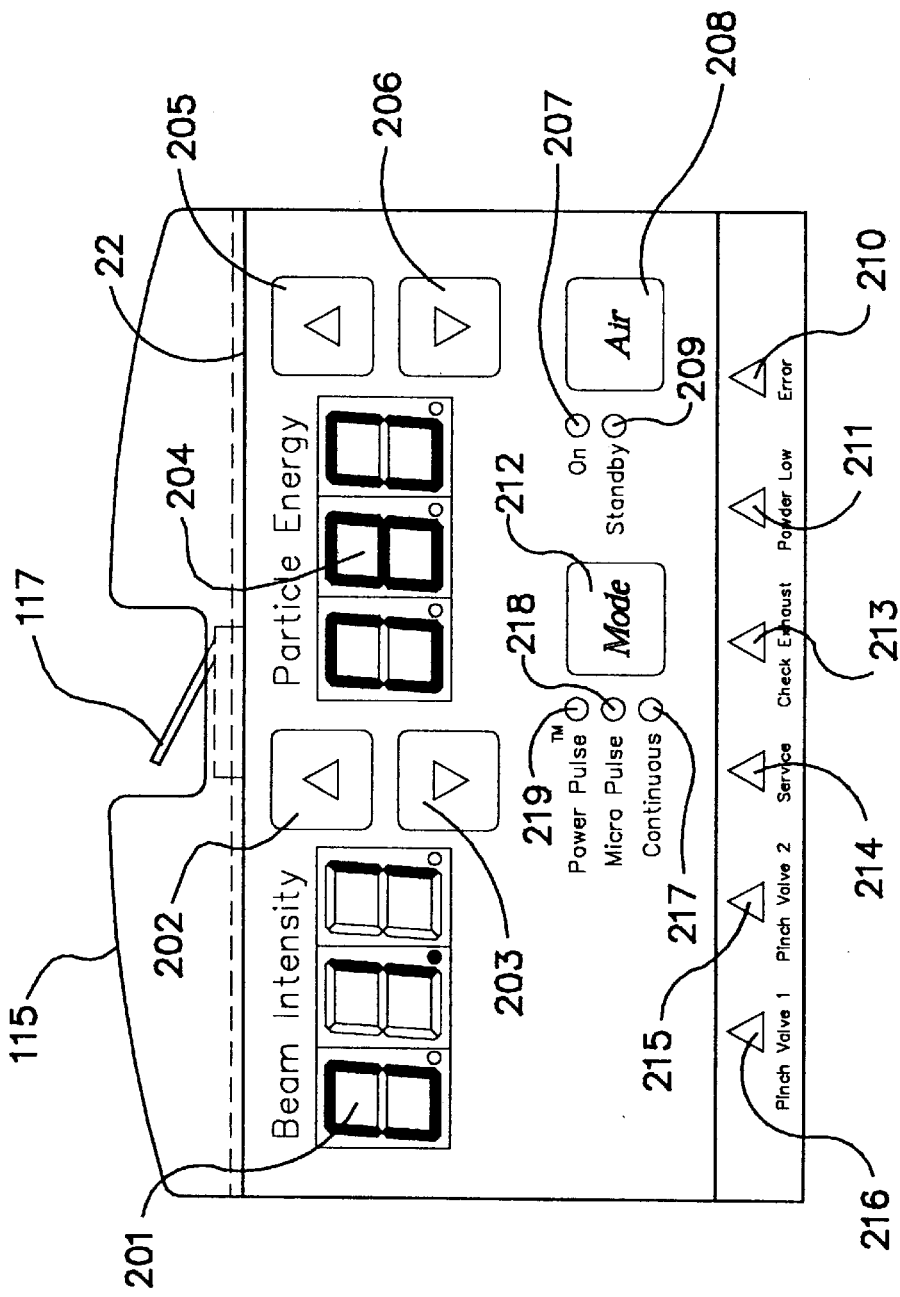
FIG. 2 is a diagram of the remote control unit of the instrument of the present invention.

The remote control unit 118 includes all warning indicators and parameter selection controls required to operate the dental instrument 1 after the dentist actuates a main power switch 24. The remote control unit 118 is small enough to fit into the palm of the hand of the dentist. As shown in FIG. 2, a control panel 22 of the remote control unit 118 serves as the user interface that allows the dentist to choose the appropriate parameter settings for the desired procedure he or she is conducting. It also allows the dentist while the dental instrument is in operation to set the loading of abrasive material in the stream (Beam Intensity) and to set the pressure of the stream (Particle Energy). Without having to move away from the patient, remote operation provides the dentist with fingertip control of the variable parameters. The dental instrument 1 is made ready for operation by depressing the "Air" button 208. By depressing the "Mode" button 212 on the panel 22, the dentist selects either a pulsed or continuous stream. A number of lights 217, 218, and 219 are illuminated to indicate the operational mode of the dental instrument, and lights 207 and 209 are, respectively, illuminated to indicate if the dental instrument is in "on" or "standby." The "on" light 207 is illuminated when the foot pedal 68 is depressed, otherwise the "standby" light 209 is illuminated.

There are warning indicators comprising a series of triangular lights 210, 211, 213, 214, and 216 along the bottom of the panel 22 which are illuminated under the control of the main central microprocessor 110 under different problematic conditions. The light 216 when lit indicates that the abrasive pinch valve 104A has malfunctioned, the light 215 when lit indicates that the dump pinch valve 104B has malfunctioned, the light 214 when lit indicates that the instrument needs service, the light 213 when lit indicates that a collection canister 109b needs to be emptied, the light 211 when lit indicates a low level of abrasive powder P in the abrasive delivery system 50 (FIG. 3), and the light 210 when lit indicates a fatal operating system error such as, for example, inadequate available pressure, leaking fluid supply lines, and the inability to reach or sustain desired voltages for the instrument's operation.

One self-monitoring safety feature of this invention is the pinch valve failure circuit. The abrasive pinch valve 104A and the bleed pinch valve 104-B are automatically monitored for operating failures by sensors 10b and 10c, respectively connected to these valves. If either one of these valves 104A or 104B develops a leak, the leaking pressure will cause an air pressure switch to close. These switches are the sensors 10a and 10b and they are electrically connected to the central microprocessor 110 over lines 10b-1 and 10c-1, respectively. The central microprocessor 110 will sense the closure and send a signal to the remote control unit 118, which will then latch the appropriate pinch valve error light 216 or 215. In order to reset the latched condition, the air mode must be switched from "standby" to "on."

A LED (light emitting diode) seven-segment display 201 indicates abrasive particle loading in the stream (Beam Intensity) and a LED seven-segment display 204 indicates stream pressure (Particle Energy). The Beam Intensity may be adjusted from 0 to 10 in increments of 1.0. The amount of abrasive in the air stream may be adjusted upward by pushing a button 202 or downward by pushing a button 203 to accommodate different particle loading according to the needs and wants of the dentist. The Particle Energy adjustment, buttons 205 and 206, controls the air pressure of the stream. When the air switch 208 is depressed to switch to "standby," and the handpiece 116 is removed from the cradle 115 so that the safety switch 117 is disengaged, the dental instrument is ready for use and is operated by depressing the foot pedal 64 with actuates a pneumatically controlled switch 121. The instrument 1 is thus switched to "on." An electrical foot switch 124 may also be provided as an optional feature. The digital display 204 shows the air pressure setting selected by the dentist. Adjustments to the dental instrument air pressure may be made by using the "up" push button 205 or the "down" push button 206 to either increase or decrease this pressure, except it cannot exceed the air pressure at the inlet 100a. The dentist may simply glance at the control panel 22, and manipulate the various control buttons, to monitor and control the operation of the dental instrument with no interruption of dental operations.

Figure 3:
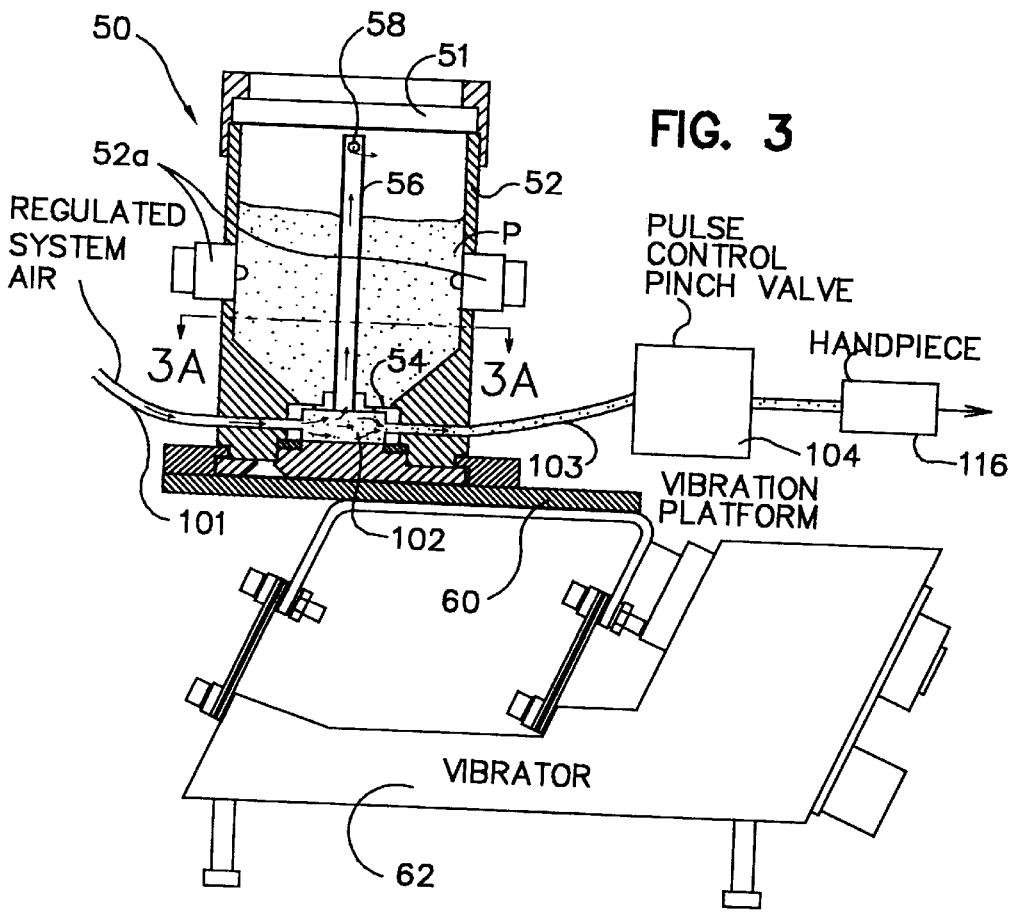
FIG. 3 is a side view, partially in cross section, of the abrasive delivery system used in the dental instrument of present invention.
Figure 3A:
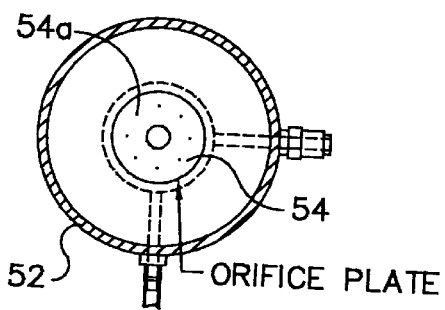
FIG. 3A is a cross sectional view taken along line 3A—3A of FIG. 3.
Figure 3B:
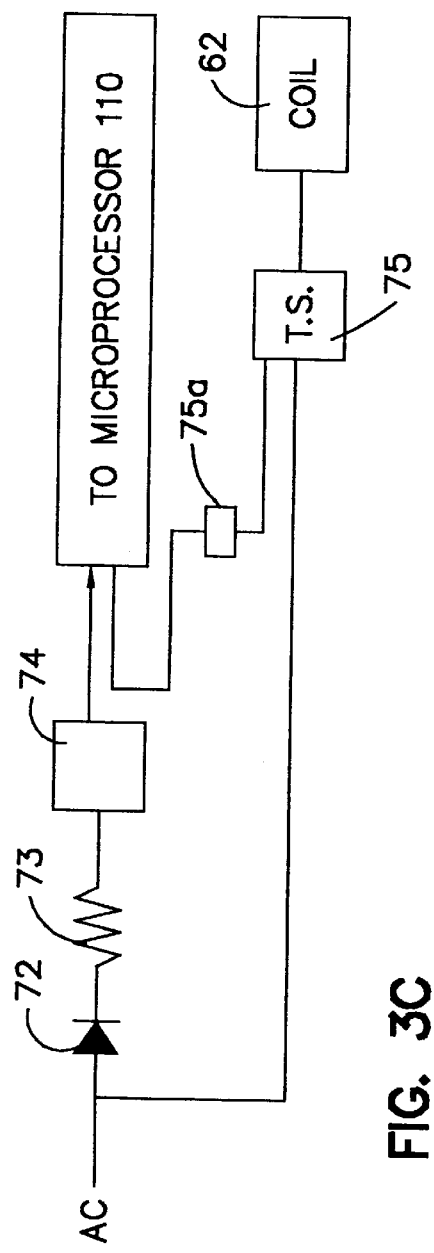
FIG. 3B is a schematic diagram depicting the manner in which the vibrator of the abrasive delivery system is actuated.

As best shown in FIGS. 3, 3A, and 3B, the abrasive delivery system 50 comprises a container 52 with a lid 51 that may be removed to add abrasive particles to the interior of the container. At the bottom of the container 52 is an orifice plate 54 with a hollow cylinder 56 extending upward from the center of the plate. There is an outlet 58 at the top of the cylinder 56 and an inlet at the bottom of the cylinder 56 which is in communication with the mixing chamber 102 which is directly below the orifice plate 54. A vibration platform 60 mounted on a vibrator 62 is rigidly attached to the chamber 52. Air under pressure from tube 101 enters the mixing chamber 102 and flows upward through the cylinder 56 to pressurize the interior of the container 52 while the vibrator shakes the platform 60 and attached container. Simultaneously, air rushes past the the orifice plate 54 with the abrasive powder P passing through holes 54a in the orifice plate to enter the stream of air exiting the mixing chamber 102 through the tube 103. This abrasive delivery system 50 relies primarily on gravity to feed particles into the air stream flowing through the mixing chamber 102. When the level of abrasive material in the container 52 is at a low level, a photoelectric eye type sensor 52a provides a control signal to the main central microprocessor 110.

Figure 1:
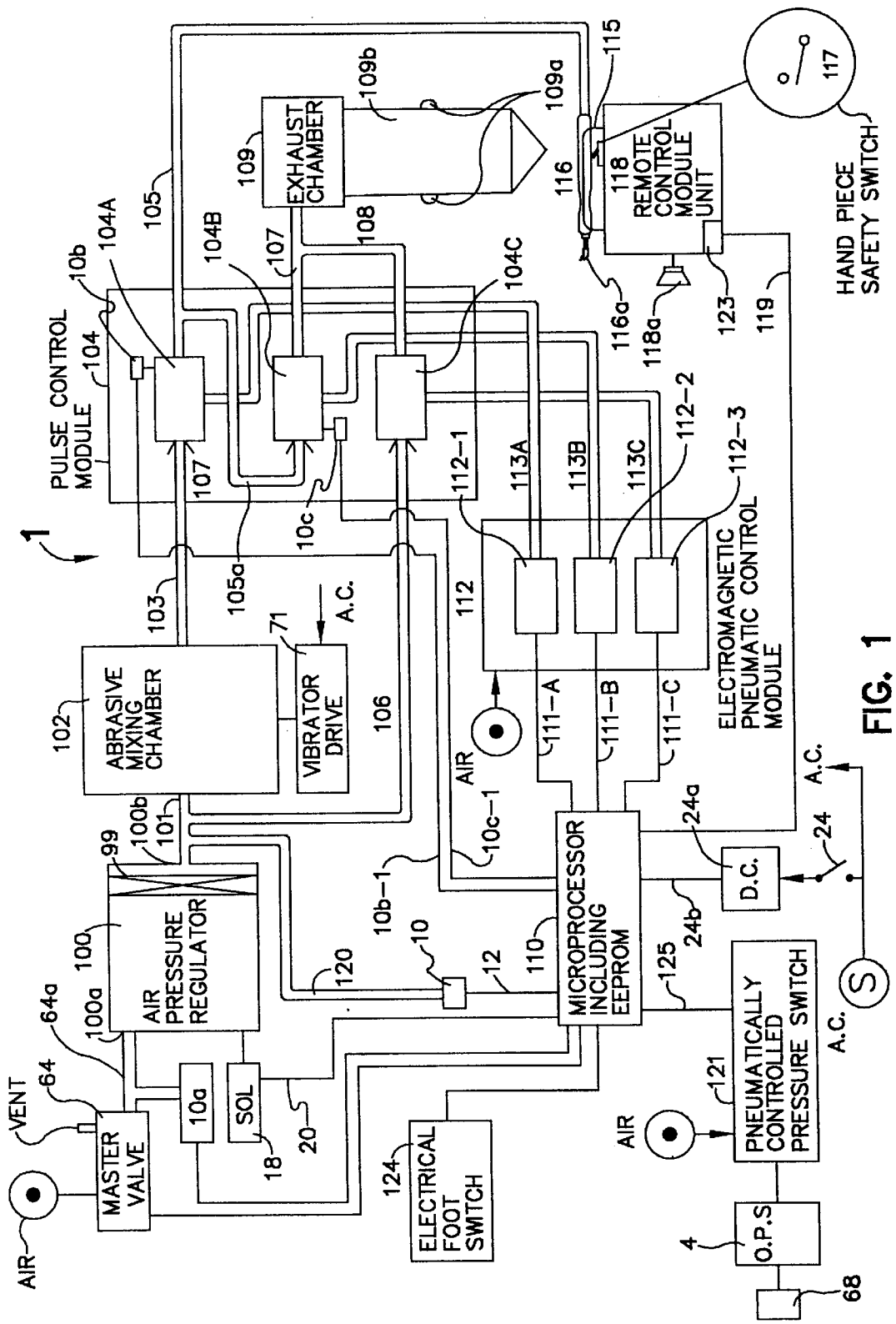
FIG. 1 is a schematic diagram illustrating the major components of the preferred embodiment of the instrument of the present invention.
Figure 3C:
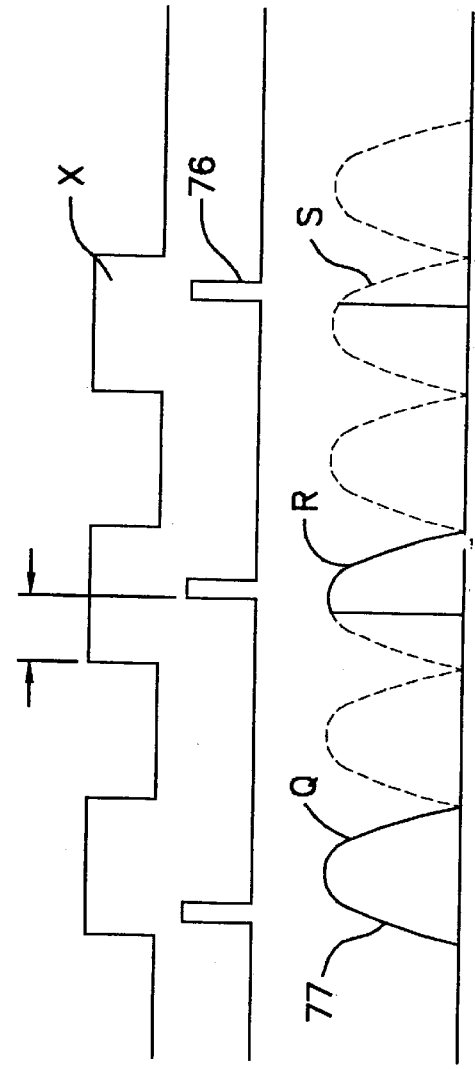
FIG. 3C is a schematic diagram depicting the character of a alternating current (A. C.) which is rectified and applied to the vibrator for the feeding abrasive powder into the mixing chamber.

FIG. 3B shows a circuit 70 for the control of the vibrator drive 71 (FIG. 1). A. C. current is rectified using a diode 72 and resistor 73 connected in series. The rectified signal 77 is depicted in FIG. 3C. An isolator 74 couples the rectified signal to the central microprocessor 110. As depicted in FIG. 3C, a square wave x at the output of the isolator 74 indicates to the microprocessor 110 the timing of the zero crossing of the rectified A. C. signal. The microprocessor 110 forwards to a thyristor switch 75, through an isolator 75a, a spike timing signal 76 which is delayed relative to the leading edge of the square wave x to regulate the vibrator drive 71. The spike signal 76 turns on the thyristor switch 75. A. C. current passes through the thyristor switch 75 to the coil (not shown) of the vibrator 62 to vibrate the platform 60. The rectified A.C. current may be modified to either increase or decrease the amount of vibration, and therefore, regulate the amount of abrasive powder P being fed into the air stream passing through the mixing chamber 102. If the spike timing signal 76 is synchronous with the rectified A.C. current, all the rectified A.C. current Q is applied to the vibrator 62. If the spike timing signal 76 is delayed slightly, a partial rectified A.C. current R is applied to the vibrator 62. If the spike timing signal 76 is greatly delayed, a greatly truncated rectified A.C. current S is applied to the vibrator 62.

Figure 4:
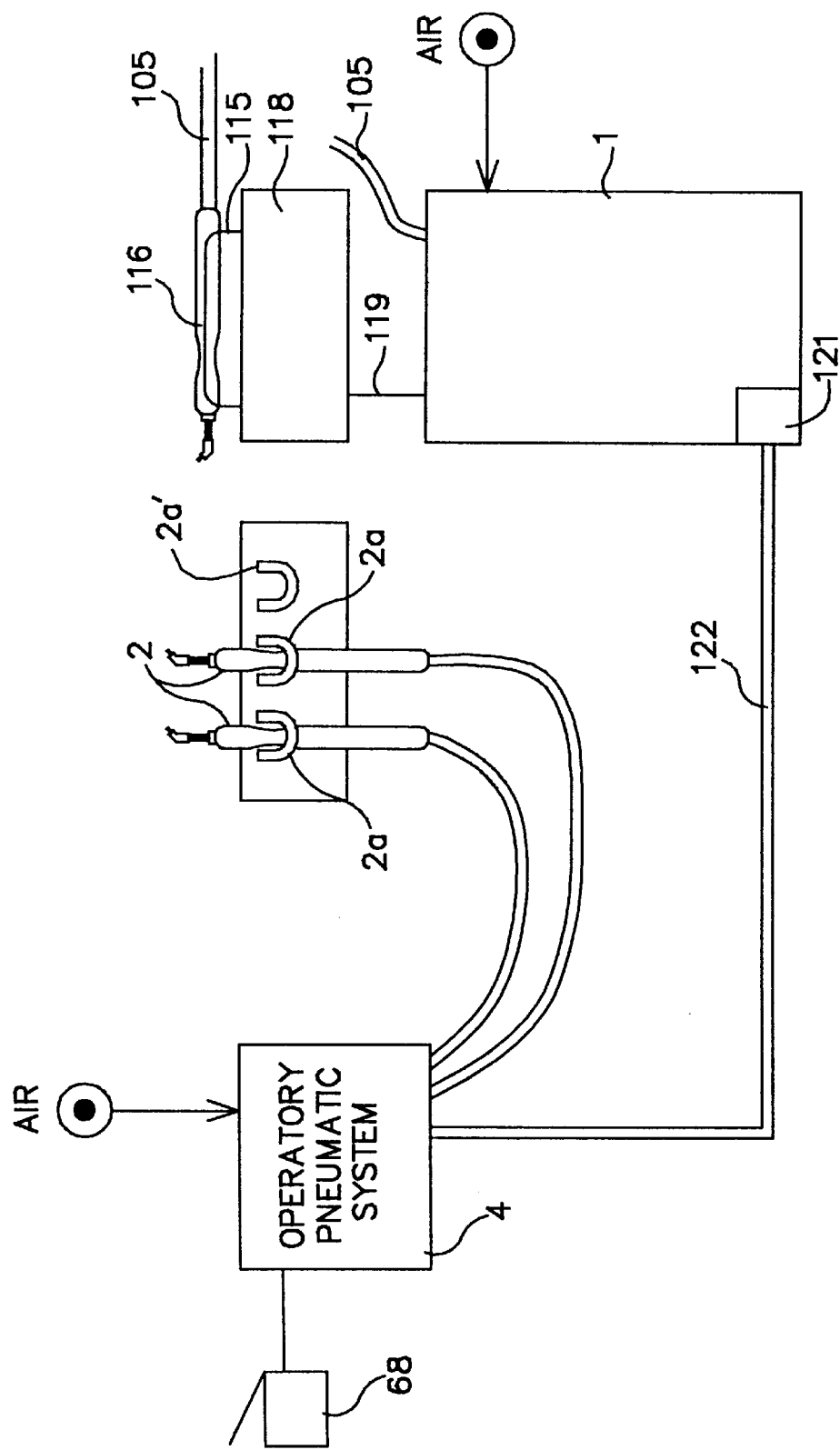
FIG. 4 is schematic diagram of the manner in which the handpiece used in the instrument of the present invention is integrated with a main dental unit foot control for a dental drill.

As illustrated in FIG. 4, the control of the handpiece 116 is integrated with the control for conventional handpieces 2 shown seated in their cradles 2a so that a foot pedal 68 used by the dentist for operation of these conventional handpieces may also be used to operate the handpiece 116. The handpiece 116 may be placed either in the empty cradle 2a' or the cradle 115 on the remote control unit 118, which is positioned adjacent the row of cradles 2a. When the foot pedal 68 is depressed, air is supplied through a conventional operatory pneumatic system 4 supplying air under pressure to all the dental handpieces, including the handpiece 116. The handpiece which is lifted out of its cradle will receive air. The dentist has the option of placing the handpiece 116 in the cradle 2a' or the cradle 115. The pneumatic pressure switch 121 of the the dental instrument 1 is connected through the tube 122 to the operatory pneumatic system 4. When the foot pedal 68 is depressed, the pneumatic pressure switch 121 closes the electrical connection that is sent to the central microprocessor 110 through line 125 (FIG. 1). When the central microprocessor 110 senses that the pressure switch 121 has been depressed, a signal sent to the remote control unit 118 through line 119 to determine if the handpiece 116 is in its cradle 115. If the handpiece is in the cradle 115, a handpiece safety switch 117 will be closed and the central microprocessor 110 will ignore the activity of the switch 121. If the dentist is using the cradle 2a' for the handpiece 116, the same result occurs. Similarly, if the handpiece 116 is not in the cradle, either the cradle 2a' or the cradle 115, foot pedal depression will initiate flow of the abrasive stream. Preferably, the central microprocessor 110 is programmed so that the handpiece 116 will only operate if all the other conventional handpieces 2 are in their cradles 2a, and the other handpieces 2 will only be operable if the handpiece 116 is in the cradle 2a' or the cradle 115.

Figure 5:
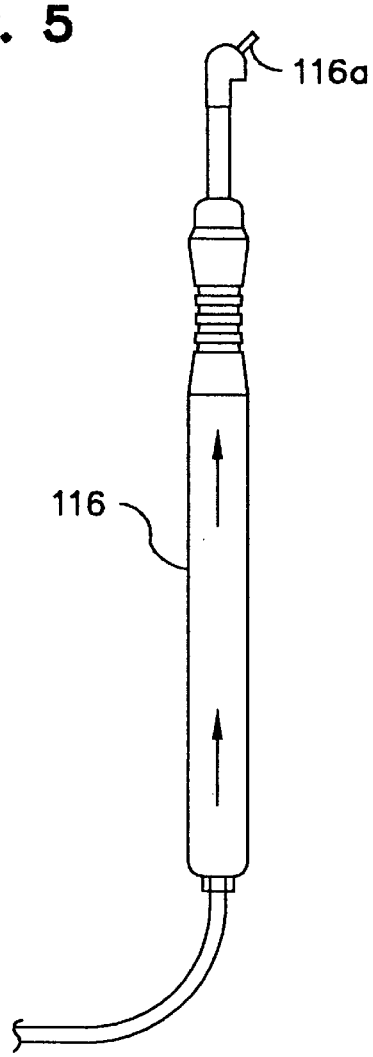
FIG. 5 is a side elevational view of a handpiece using a supersonic nozzle.
Figure 6:
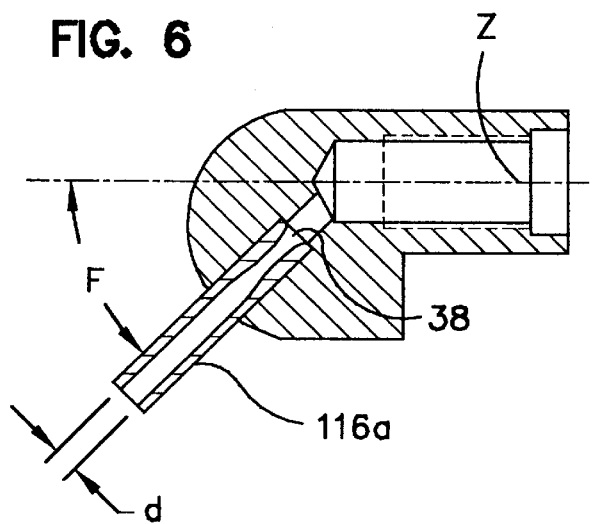
FIG. 6 is a cross-sectional view of the nozzle end of the handpiece shown in FIG. 5.

FIGS. 5 and 6 illustrate a supersonic nozzle 116a for the handpiece 116. This nozzle 116a is disclosed in U.S. patent application Ser. No. 08/821,976, filed Mar. 13, 1997, and entitled Supersonic Converging-Diverging Nozzle For Use On Biological Organisms, which is incorporated herein by reference and made a part of this application and which is owned by Kreativ, Inc., the assignee of the present application. As discussed in detail in this co-pending patent application, the nozzle 116a is connected to an outlet in a head assembly 20, and it includes a passageway 38 with a converging-diverging internal shape. This nozzle 116a may be oriented at several different angles F with respect to the axis Z of the head assembly 20. Nozzle angles F of 45°, 67°, or 90° have been used successfully. As discussed in greater detail in connection with the EXAMPLES, the diameter d of the outlet end of the nozzle 116a typically ranges from about 0.01 inch to about 0.03 inch. For example, the diameter d may be 0.018 inch diameter nozzle to remove large lesions and existing restorations, a 0.014 inch diameter nozzle for most small lesions, or a 0.011 inch diameter nozzle for very precise cutting, diagnosis of occlusal pits and fissures, incipient Class II and III lesions or for placing fine retention in Class IV and V restorations.

OPERATION OF DENTAL INSTRUMENT

To operate the dental instrument 1, the dentist first switches on the main power switch 24 and depresses the button 208. This applies power to the central microprocessor 110 through a D. C power supply 24a. The dental instrument 1 is now in "standby" and the light 209 is illuminated. The last pressure selected by the dentist is displayed on the display 204, and the last abrasive loading of the stream selected by the dentist is displayed on the display 201. If the dentist wishes to make changes in either of these parameters, he or she manipulates the suitable control buttons 202, 203, 205 and 206. Depressing the foot pedal 68 actuates the switch 121 and illumination of the "standby" 209 is discontinued and the "on" light 207 is illuminated. Prior to switching to "on," the valves 104A, 104B and 104C are all closed as determined by the central microprocessor 110 providing appropriate control signals over the lines 111-A, 111-B, and 111-C to the appropriate solenoids 112-1, 112-2, and 112-3 in the electromagnetic pneumatic control module 112, so that the system pressure is applied to the valves 104A, 104B and 104C. Each solenoid 112-1, 112-2, and 112-3 controls a valve (not shown) respectively in the tubes 113A, 113B, and 113C. With any one of these solenoid controlled valves open, the pressure in the tube it is connected to will be at atmospheric pressure. When the solenoid controlled pneumatic valves are closed, the tubes 113A, 113B, and 113C are at the internal pressure of the dental instrument 1. The central microprocessor 110 in response to the normal fluctuations of internal system pressure caused by the valve 104A opening and closing when in one of the pulsed modes, or remaining open in the continuous mode, operates the "on/off" valve 99 in the air regulator 100 to achieve and maintain the selected stream pressure as air leaves the system each time the foot pedal 68 is depressed.

The dental instrument 1 is an open looped system and the pressure of the system is not preset, but returns to ambient air pressure each time the instrument is turned off. Thus, when the dental instrument 1 is switch to "standby," the internal pressure of the system must be increased from ambient pressure to the pressure selected by the dentist. If, for example, the dentist wishes to operate at a stream pressure of 100 psi, he or she will repeatedly depress the button 205 until the display 204 shows 100. As soon as the dentist switches to "standby" by pressing the button 208, the central microprocessor 110, in response to the pressure sensed by the sensor 10, energizes the solenoid 18 in short electrical bursts to open and close the "on/off" valve 99 of the air regulator 100 rapidly until the internal system pressure of the dental instrument 1 is equal to 100 psi. If the limits of the instrument ar exceeded, the beeper 118a is energized by the program for the main central microprocessor 110.

The dentist may now operate the handpiece 116 lifted from the cradle 115 by stepping on the foot pedal 68. As long as the foot pedal 68 is held down, a stream of particle laden air exits the nozzle 116a of the handpiece 116. If the dentist has selected either the Power Pulse or Micro Pulse mode, the stream will be pulsed by the valve 104A opening and closing at the selected pulse duration. If the dentist has selected the Continuous mode, the valve 104A remains constantly open and the stream is continuous as long as the foot pedal 68 is depressed. The stream exits the valve 104A and flows through the tube 105 to the handpiece 116 and out the nozzle 116a. In the dental instrument 1, the dentist may selectively increase or decrease the stream pressure as desired, or switch from pulsed to continuous and vice versa, as desired. The internal pressure of the instrument 1 is sensed by the sensor 10 and the central microprocessor 110 takes the necessary measures to accommodate the changes called for as discussed subsequently.

When the dentist releases the foot pedal 68, the switch 121 changes states and this condition is sensed and a control signal is forwarded to the central microprocessor 110 over the line 125. Signals are then forwarded by the central microprocessor 110 over the lines 111A and 111B to the electromagnetic pneumatic control module 112, respectively, (a) to deenergize the solenoid 112-1 which closes its valve (not shown) to connect the tube 113A to internal instrument pressure and (b) to energize the solenoid 112-2 which opens its valve (not shown) to connect the tube 113B to ambient air pressure. This actuates the valve 104A, closing it, and actuates the valve 104B, opening it, to place the tube 107 in communication with a collection cannister 109b having at its inlet an exhaust chamber 109 connected to the line 107. Since ambient pressure is lower than the instrument's pressure, air and particulates in the tube 105 are drawn through the branched tube 105a and tube 107, into and through the exhaust chamber 109, with any particles in the air collecting in the canister 109b. A sensor 109a detects the level of powder in the canister 109b, and provides a control signal to the central microprocessor 110 when the canister needs to be dumped. No materials from the patient's mouth are drawn into the nozzle 116a. This back flow of air through tubes 105 and 105a prevents undesired burping (extraneous eruptions of abrasive fluid) from the handpiece 116. The valve 104C remains closed to maintain the instrument's pressure at the pressure selected by the dentist.

If the dental instrument 1 is (1) shut down by the dentist turning the power switch 24 "off," or (2) the pressure of the instrument is reduced by the dentist pushing the button 206, both the valves 104B and 104C are opened. As discussed above, the opening of valve 104B is controlled and functions as before under these conditions. When the power switch 24 is turned "off," the central microprocessor 110 detects this condition by a signal forwarded over the line 24b. The central microprocessor 110 then provides a control signal over the line 111-C to the solenoid 112-3 that switches its valve (not shown) to ambient pressure which is applied through the tube 113C to the valve 104C to open this valve. Opening the valve 104C vents the instrument of pressurized air which escapes through the tubes 106,108 and 107 out the exhaust chamber 109. The internal pressure of the dental instrument 1 is now at ambient pressure and must again be pressurized upon starting the instrument.

When the pressure of the stream is reduced by depressing the button 206, the valve 104C is opened. The sensor 10 detects that the internal pressure is above the pressure selected by the dentist, and this provides a signal to the central microprocessor 110 to open valve 104C as discussed above. As air escapes from the instrument, the valve 104C remains open until the instrument's pressure equals that selected by the dentist. When this selected reduced pressure is reached, the valve 104C is closed by the central microprocessor 110 signalling the solenoid 112-3 to position its internal valve (not shown) so that the pressure applied to the valve 104C is the reduced internal pressure, thus closing this valve 104C. The central microprocessor 110 then in response to the normal fluctuations of pressure caused by the valve 104A opening and closing when in one of the pulsed modes, or being opened constantly in the continuous mode, operates the "on/off" valve 99 of the regulator 100 to maintain the reduced stream pressure.

MICROPROCESSOR

The central microprocessor 110 provides digital control signals as opposed to analog control signals and is programmed in accordance with conventional programming techniques with the routines to be preformed illustrated in FIGS. 8 and 8A. These routines will be discussed in greater detail subsequently. The preferred microprocessor is manufactured by Microchip Technology, Inc. and identified as PIC16C74A. One advantage in using the central microprocessor 110 to control the instrument 1 is that it may be readily replaced with another microprocessor for repair of the instrument or for even reprogramming the instrument to preform differently than the original program.

Figure 7:
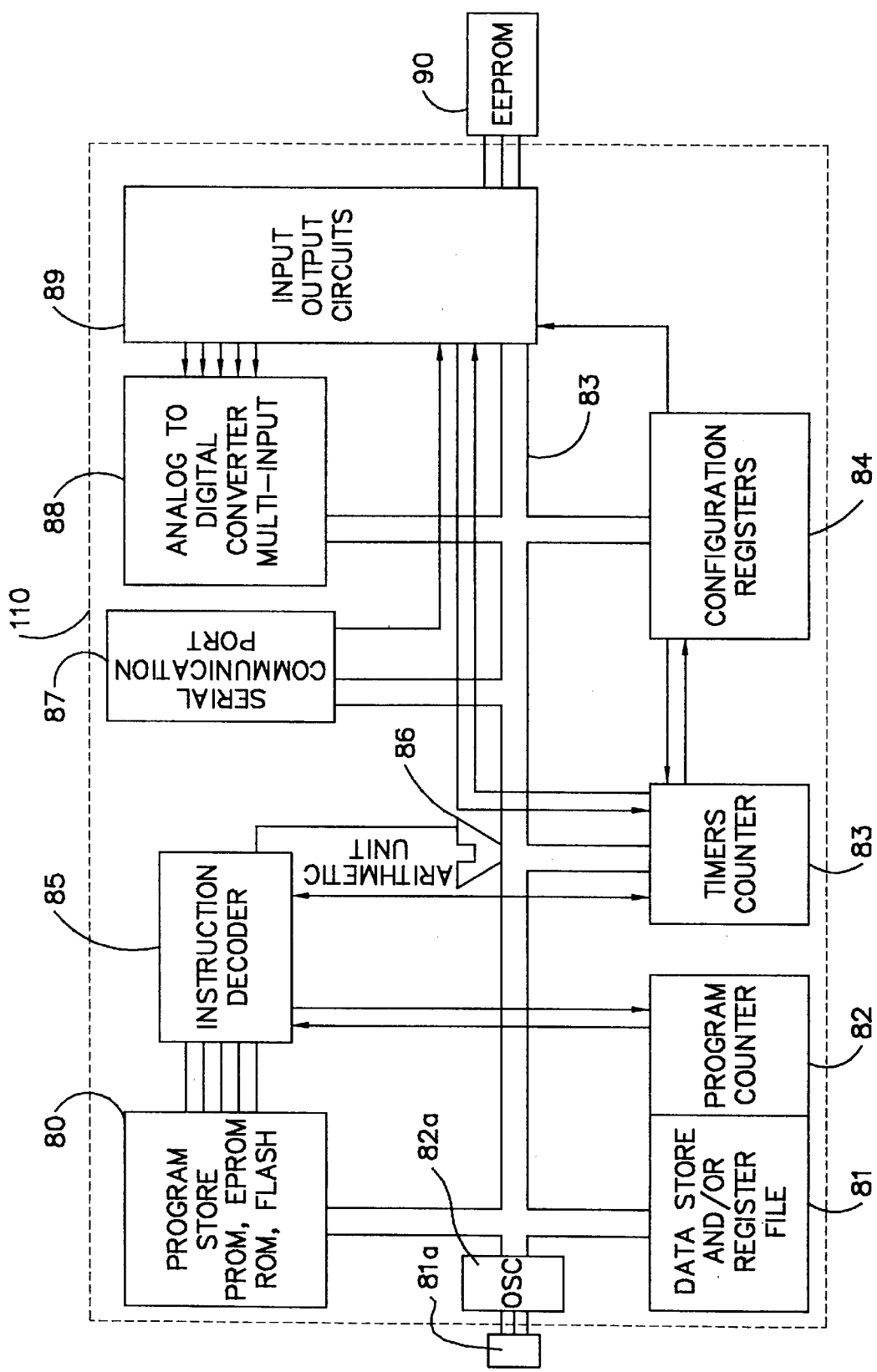
FIG. 7 is a schematic block diagram of the main central microprocessor circuit used in the instrument of the present invention.

As illustrated in FIG. 7, the central microprocessor 110 includes a bus 83 to which are electrically connected the major components of the microprocessor, including program storage memory 80 having memory components such as a PROM, EPROM, ROM, FLASH, etc. (not shown), data storage memory 81 including various registers, a program counter 82, utility timers and counters 83, configuration registers 84, instruction decoder 85, arithmetic unit 86, serial communication port 87, an analog to digital converter 88, and input-output circuits 89. There is an external crystal resonator 81a connected to an internal oscillator 82a which determines the rate of execution of instructions for the program. The oscillator 82a further provides the time base required by the utility timers and counters 83, serial communication port 87, and analog to digital converter 88. An EEPROM 90, which provides a non-volatile read-write memory, is connected between the input-output circuits 89 and the remote microprocessor 123 in the remote control unit 118. Intermediate settings are forwarded to the data storage memory 81 when manipulating the buttons 202, 203, 205, and 206 to vary the abrasive loading and pressure of the stream and these intermediate settings are eventually erased. As the user manipulates the buttons 202, 203, 205, and 206, the last setting is stored in the EEPROM 90, so that when the instrument 1 is turned off and then turned on again, this last setting will be automatically programmed in the remote control unit 118.

The remote microprocessor 123 is substantially similar to the main central microprocessor 110. The principal difference is that it is physically smaller, since it does not include the analog to digital converter 88. Therefore, it conveniently fits within the compact remote unit 118. This microprocessor 123 is also manufactured by Microchip Technology, Inc. and identified as PIC16C62A.

PROGRAM

The program routines for the main central microprocessor 110 are represented by the logic flow diagrams of FIGS. 8 and 8A. In the start-up routine 500, the central microprocessor 110 powers up several registers (not shown) and latches (not shown) which are set to standard settings determined by the microprocessor's manufacturer. Upon completion of the start-up routine 500, the program, in accordance with the routine 501, configures input/output circuits 89 and timer circuits of the data storage memory 81 as needed to respond to the sensors 10, 10a, 10b, 10c, 52a, and 109a, enables the remote control unit 118, checks the 50/60 Hz line frequency for the vibrator 62, enables the pressure sensor 10, and recalls the last setting of the remote control unit 118 from the EEPROM 90. A diagnostic check is also preformed to confirm that the instrument 1 is set for operations, and if not, the triangular error light 210 is illuminated. A message will be shown on the display 204 to indicate the type of error occurring.

To complete the start-up, the main central microprocessor 110 enters a main loop to monitor idle conditions and respond to the commands of the routine 502. In the routine 502, the signals from the remote control unit 118 are received, the information to be displayed on the the displays 201 and 204 is forwarded to the remote control unit 118, and the remote control unit 118 is switched to "standby" if the foot pedal is not engaged for several minutes, for example, 2 minutes. The pinch valve sensors 10b and 10c and powder level sensors 52a and 109a are monitored in accordance with the routine 503 and the central microprocessor 110 provides intermittent control signals. The central microprocessor 110 through the sensor 10 detects the internal pressure of the instrument 1 and signals the valve 104C to open if the pressure needs to be lowered.

The multiple functions of the control panel 22 are under the control of the routine 504. Included among these are the abrasive loading and the stream pressure set by manipulation of the buttons 202, 203, 205, and 206, the desired Mode set by the button 212, and standby set by the button 209.

The routine 505 responds to the conditions detected by the sensor 10 to open and close the valve 99 in the air pressure regulator 100 to establish the pressure selected by the user manipulating the buttons 205 and 206. If stream pressure (Particle Energy), abrasive loading (Beam Intensity), or operating Modes (pulsed or continuous) have been changed during the routine 505, the new values are written to the EEPROM 90 in accordance with the routine 506.

In accordance with the routine 507, the foot switch 124, the pressure sensor 10, and the safety switch 117 on the cradle 115 for the handpiece 116 are tested, and the buttons 202, 203, 205, 206, 212, and 208 are released. If the operating conditions are valid and a demand for abrasive flow 507 is made by depressing the foot pedal 68, the routine 508 starts abrasive flow through the routine 509. If operating conditions are not valid or the foot pedal is not depressed, the idle state is continued.

The routine 510 calls upon the central microprocessor 110 to prepare conditions for stream flow. The flow will be either continuous or pulsed according to the user's selection of parameters through the remote control unit 118. Routine 511 will monitor and regulate pressure according to the user settings in accordance with the routines 504 and 506. The routine 512 monitors the instrument's safety conditions. It will exit to the error handler routine 517 in the event that the voltage supply is outside the desired range, excess pressure, closure of the safety switch 117, a disconnect occurs between the central microprocessor 110 and the remote control unit 118, or other problems.

Routine 513 opens and closes the valve 104A as determined by the user setting the parameters using the remote control unit 118. The vibrator 62 is energized by this routine 513 when the valve 104A is open. Routine 514 senses the signals from the remote control unit 118, and continually updates the signals being provided if the user changes a setting while operating the instrument 1. Thus, the user may change, for example, the abrasive loading or stream pressure using the the remote control unit 118, and the appropriate changes will be made to adjust for the new settings. Routine 514 also detects failures of pinch valve 104A and 104B. If the user does not depress the foot pedal 68 within a predetermined time, for example, 2 minutes, the instrument will be switched to "standby." Routine 514 will also check to determine if air valve 99 is still on, the handpiece 116 has been returned to cradle 115, and will cause the "low air" message to light the displays 201 and 204, if necessary. Routine 515 senses if the footswitch 121 is activated. Routines 511 through 515 are repeated about 2000 times per second during the instrument's operation. With the release of the foot pedal 68, abrasive feeding is stopped by routine 516.

The air pressure regulator 100 is controlled by the routines 520, 521, 522, 523, and 524, and 525. The pressure as monitored by the sensor 10 is compared to the desired setting through the routines 520, 521 and 522. If the desired pressure is reached, no action is taken by routine 523. As these routines 520, 521, and 522 are repeated at a high rate of speed, the valve 99 in the regulator 100, opening and closing rapidly, remaining open for a duration ranging between 0.3 to 0.6 milliseconds, will remain closed when the desired pressure is reached as called for by routine 524. As called for by the routine 525, the abrasive delivery system 50 remains idle or resumes delivering abrasive particles in accordance with the routines 510 through 515.

The error handler routine 517 shuts off all the valves 64, 99, 104A, 104B, and 104C through routine 518, de-energizes the vibrator 62, illuminates the error light 210, and identifies the error condition as a number which is shown on the display 204 of the remote control unit 118. If the error is not a severe, the routine 519 exits to idle state. For severe errors, power is discontinued to the instrument 1. Severe errors include, for example, power supply malfunction, the microprocessor timer cannot be set, the pressure sensor 10 malfunctions, or the vibrator drive 71 malfunctions. Non-severe errors include, for example, inability to recall settings from the EEPROM 90, accidental disconnection from the main central microprocessor 110 of the remote control unit 118, or the remote control unit 118 or one of the valves 104A–104C is leaking.

The control of the audio alarm, beeper 118a, is achieved through the sub-routines illustrated in FIG. 8A. Routine 504 includes the sub-routines 550, 552, and 554. The sub-routine 550 determines if any one of the buttons 202, 203, 205, or 206 is being depressed by the user. If not, the buttons are in the reset state and the program advances to the next routine 505. If yes, the program advances to the next sub-routine 552, which determines if the user has selected a value which exceeds the limits of the instrument. For example, if the dentist depresses the buttons 205 or 206 so that the air pressure is outside the range of 20 to 120 psi, the sub-routine 552 would provide a signal to energize the beeper 118a and illuminate the error light 210. The same would be true if the button 202 was used to set the particle loading above 10, the maximum of 10 grams per minute. If not, the program advances to the next sub-routine 554, which allows the settings of the air pressure to be changed either one unit at a time or in units of five when one of the buttons is 205 and 206 are held down by the user. Upon reaching the selected setting, the sub-routine 554 advances to the routine 505.

Routine 507 includes the sub-routines 556, 558, and 560 for activating the beeper 118a when the safety switch 117 has not been released by lifting the handpiece 116 from its cradle 115. If the sub-routine 556 indicates that the foot pedal 68 has not been depressed, the program advances to the routines 508 through 502. If yes, it advances to the sub-routine 558 which checks to determine if the air is available and the air indicator light 207 is "on." If no, the program advances to the routines 508 through 502. If yes, it advances to the sub-routine 560, which checks to see if the handpiece 116 has been lifted from the cradle 115 to release the safety switch 117. If not, the beeper 118a is activated and the error light 210 illuminated. If yes, the program advances to the routines 508 through 509.

Routine 525 consists of the sub-routines 562 through 576 for confirming proper operation of the regulator 100 warning the user of low pressure, and protecting the patient from excessive pressure. If the user has selected a pressure using buttons 205 and 206 higher than that which is available at the master valve 64 or which will pass through the air tubes, the regulator routine 525 will continue to energize the regulator 100, so that its continuous operation is detected in accordance with routine 562 after which the air pressure sensor 10 is compared to the desired setting in accordance with routine 564. It may be that the supply pressure or tube pressure is just adequate in which case no error condition is to occur, and a beeped-flag is cleared in accordance with routine 563. If the delivery pressure is indeed too low, however, and the beep has not yet been signaled in accordance with a test of the beeped-flag in routine 566, then the beeper 118a is beeped, and the beeped flag is set. This use of the beeped-flag prevents a continuous beep from being heard if the user persists in operating at low pressure. Whether the beeper 118a is activated or not, the message "Lo Air" is sent to the displays 201 and 204 in accordance with instructions from the central microprocessor 110 which are forwarded to the remote microprocessor 123. The regulator valve pattern is again examined in accordance with routine 568. If the regulator valve 99 is operating on and off, the beeped-flag is cleared in accordance with routine 563. If the regulator valve 99 remains off in accordance with routine 523, the pressure is compared to the setting in accordance with routine 570. If the pressure is within the pressure setting in accordance with buttons 205 and 206, subroutine 525 ends and the ready state (routines 502–508) or stream flow state (routines 511–515) resumes. Otherwise the ready or stream flow state of the instrument is determined in accordance with routine 572. If in stream flow mode, then the regulator 100 has been passing more air than required by the stream resulting in the excess which transfers control to the error handler 517, shuts off master air valve 64, and issues an error message. If the instrument is in ready mode (no stream flowing) pressure is relieved by opening valve 104c in accordance with routine 574 for a fixed period of 100–500 milliseconds. If the valve 104c failed to relieve pressure, the pressure sensor 10 will still have an excessive value as determined by routine 576, transferring control of the program to the error handler 517, shutting off the master air valve 64, and issuing an error message.

The program routines for the remote microprocessor are represented by the logic flow diagram of FIG. 10, and they are designed to signal the central microprocessor 110 in accordance with the operation of the handpiece safety switch 117 and push buttons 202, 203, 205, 206, 208, and 212. Individual segments of the displays 201 and 204 and the triangular warning lights 210, 211, 213, 214, 215 and 216 are illuminated in accordance with instructions from the program from the central microprocessor 110 which are forwarded to the remote microprocessor 123.

The program routines for the remote microprocessor are represented by the logic flow diagram of FIG. 10. The routine 600 configures output ports for the LED display drivers (not shown), and input ports for safety switch 117 and the buttons 202, 203, 205, 206, 208, 212. The routine 600 further sets the timing functions (a) for serial communication with the microprocessor 110, and (b) for the rate at which display digits are multiplexed and button states are sampled. In routine 600 all the LEDs are enabled and lit for one second so that the user may observe that they are functional. The beeper 118a is also briefly activated so that the user may observe that it is functional and that power has been turned on.

The routine 602 compares the current state of the buttons 202, 203, 205, 206, 208, 212 to a previous state sampled several milliseconds earlier, preferably from about 10 to about 20 milliseconds. Likewise the current state of the safety switch 117 is compared to a previous state sampled several milliseconds earlier. If there is a change in the button state, a predetermined numeric code identifying which individual button has changed state and whether the the button is activated or deactivated. This information concerning the state of the buttons is transmitted to the microprocessor 110. The state of the switch 117b is similarly tested and its state of activation is transmitted to the central microprocessor 110. Signals from the central microprocessor 110 are forwarded to the remote microprocessor independently of receiving updated information from the remote microprocessor. In routine 606 the central microprocessor 110 transmits a signal to either activate the alarm or signals to update anyone or all of the displays 201 and 204 on the panel 22.

MULTIPLE OPERATORIES

Figure 9:
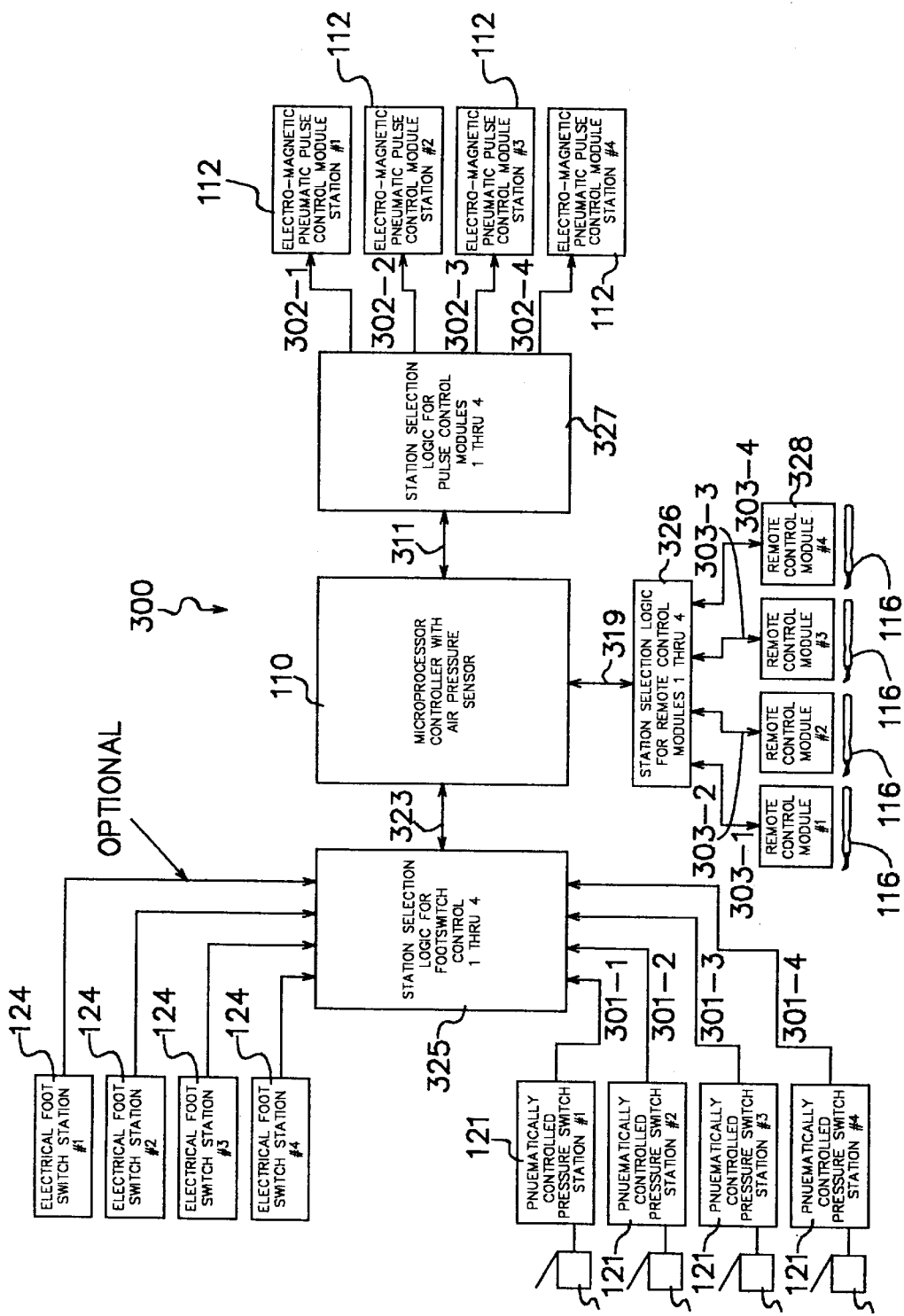
FIG. 9 is a block diagram of the individual remote control units at separate operatories, with the individual remote control units being control by a remote central control unit including the main central microprocessor.

A problem that has been associated with the practice of air abrasion dentistry is the large size of the unit in relation to a relatively small dental office. Placing a large device close to the patient may occupy valuable floor or counter space. In this invention as illustrated in FIG. 9, an individual remote control unit 118 for separate operatories #1, #2, #3, and #4 may be hard-wired or otherwise connected to a central control unit 300 to control the parameters of the handpiece 116 associated with each remote control unit 118. Doing this allows the central control unit 300 to be placed anywhere space is available to control a plurality of handpieces 116, each located in the different operatories #1, #2, #3, and #4. This increases the efficiency and cost effectiveness of the dental instrument of this invention for small dental practices.

FIG. 9 shows an office with the multiple operatories #1, #2, #3, and #4, each equipped with a remote control unit 303-1, 303-2, 303-3, and 303-4, respectively, and each equipped with a pneumatically controlled pressure switch 121 operated by individual foot pedals A, B, C and D, respectively, at each operatory. In addition to the central microprocessor 110, although not shown in FIG. 9, the central control unit 300 contains all associated electronics and sensors used with the microprocessor 110, the air pressure regulator 100, the pinch valves 104A through 104C, the abrasive delivery system 50, and the exhaust chamber 109. Tubing (not shown) extends from the central control unit 300 to the individual handpieces 116, respectively associated with each remote control unit 303-1, 303-2, 303-3, and 303-4 at each individual operatory #1, #2, #3, and #4. Optionally, instead of using pneumatically controlled pressure switches 121, electrical foot switches 124 may be used in their place.

The single office dental instrument 1 shown in FIG. 1 is easily modified using its main central microprocessor 110 to provide individual control of each handpiece 116 at each separate operatory #1, #2, #3, and #4 of the multiple operatory system. Each handpiece 116 at each individual operators #1, #2, #3, and #4 has its own own electromagnetic pneumatic control module 112. The central microprocessor 110, through station selection logic for footswitch controls 325, station selection logic for pulse control modules 327, and station selection logic for remote control units 319, controls the operation of each handpiece 116 in each individual operatory #1, #2, #3, and #4 in accordance with the settings selected by the dentist manipulating the buttons 202, 203, 205, 206, 208, and 212 of the remote control unit in each operatory.

The central microprocessor 110 is able to select any one, or any combination, or all four of the four different operatory #1, #2, #3, and #4 by signaling to the station selection logic modules 325, 326, and 327. The microprocessor sends a station select signal to the foot switch selection module 325 through line 323. In a similar fashion, the central microprocessor 110 sends a signal to the remote control selection module 326 through line 319. Likewise, the central microprocessor 110 signals the pulse control selector 327 through line 311. From the signal sent by the central microprocessor 110, the foot switch control selection mode 325 then selects the appropriate pneumatic pressure switch 121. The pneumatic pressure switches 121 are connected to the control module 325 through lines 301-1, 301-2, 301-3, and 301-4. Actuation of one of the foot pedals A, B, C and D operates an associated pneumatic pressure switch 121. Then the selection logic 325 relays the switch closure to the central microprocessor 110. The remote control selection module 326 then selects the appropriate remote control unit 303-1, 303-2, 303-3, and 303-4, which are connected to the selection module through paths 303-1, 303-2, 303-3, or 303-4, respectively. The pulse control selection module 327 then selects the appropriate electromagnetic pneumatic pulse control module 112. The selected electromagnetic pulse control module signal is forwarded to the control module 327 through the lines 302-1, 302-2, 302-3, or 302-4.

EXAMPLES

As illustrated in the following in the Examples, the various parameters and conditions necessary for various dental procedures are disclosed. It is generally recommended to use the lowest air pressure possible for a given procedure. It is also important to select a nozzle size suitable for the particular procedure. The larger the nozzle, the larger the cavity or hole it creates. More specifically, a 0.018 inch nozzle would be used to remove large lesions and existing restorations, and a 0.014 inch nozzle for most small lesions. The 0.011 inch nozzle is suitable for very precise cutting, such as diagnosis of occlusal pits and fissures, incipient Class II and III lesions or for placing fine retention in Class IV and V restorations. The nozzles that are used with the instant invention are pitched at different angles. The nozzle angle that provides the best access to the tooth of interest should be selected. This choice will be easily made by the operating dentist. Most preparations can be performed with a 45° angled nozzle, but 67° or 90° angles usually allow better access to maxillary molar occlusal surfaces and lingual surfaces of maxillary anterior teeth. A common choice among dentists is the 45° angle 0.014 inch nozzle for most procedures. The supersonic nozzles available for use with the instrument 1 effectively doubles the particle speed at a given air pressure. When the desired operation is removal of spent amalgam, the supersonic nozzle is preferred for use with the instrument 1. Example 6 provides further details of the procedure for amalgam removal.

The following examples are meant for illustrative purposes only and are not intended to limit the instant invention in any manner whatsoever. Examples 1–6 present a description of actual dental operatory conditions for optimal use the dental air abrasion unit of this invention for various dental operations. Included are examples of preparing teeth for veneer/facing restorations, preparing teeth for pit and fissure sealants, partial or complete removal of composite restorations, repair of failures sites of composite restorations, etching metal, porcelain, or composite restorations prior to repair, removing stains and other cleaning operations, and removal of spent amalgam. Since the following are meant to be illustrative examples, the dentist who desires the use of abrasion techniques in his or her practice will be able to modify these procedures to individual needs, preferences, and patient comfort.

Example 1

Preparing Teeth for Veneer/Facing Restoration Using the Instrument of this Invention, available commercially as dental instrument Mach 5.0, made by Kreativ, Inc.

| Operating Conditions: | |
|---|---|
| Particle Energy | 40–60 psi |
| Abrasive Powder | Aluminum Oxide 27.5 micron GammaPure ™ |
| Beam Intensity | 3–5 grams/minute |
| Mode | MicroPulse ™ |
| Nozzle Diameter | 0.018 inch |
| Time | 5–10 seconds/tooth |

Procedure: The unit of this invention is indicated to remove pellicle, temporary cement or filling material, plaque, and stain from prepared teeth prior to bonding. Place the nozzle at a proper distance to remove the smear layer and clean, but not cut, the surface. The unit of this invention may be used to provide the ideal polished bevel at the restoration margins or to provide the veneer preparation. These conditions are not indicated to replace acid etching for bonding. It should be noted that air abrasion will not "remove" the smear layer from dentin but rather creates one. Acid etch must be used in this procedure to remove the dentin smear layer prior to bonding.

Example 2

Preparing Teeth for Pit and Fissure Sealants using the Instrument of this Invention

| Operating Conditions: | |
|---|---|
| Particle Energy | 40–60 psi |
| Abrasive Powder | Aluminum Oxide 27.5 micron GammaPure ™ |
| Beam Intensity | 3–5 grams/minute |
| Mode | MicroPulse ™ |
| Nozzle Diameter | 0.011 inch Standard or SST |
| Time | 5–10 seconds/tooth as required |

Procedure: The air abrasion unit of this invention is indicated for removal of the organic plug and stain for pit an fissure sealant preparation. Care must be taken to not spend too much time with the nozzle in one area as unintentional cutting could result. The nozzle is kept at the center of the pit and fissure and moved in a continuous slow sweeping motion to clean the pit and fissures. The procedure is continued with traditional acid etching and restorative techniques.

In the process of debridement, if any decay is present the air abrasive unit of this invention will selectively and quickly remove areas of demineralized enamel and dentin. This adds to the accurate diagnosis of pit and fissure caries, resulting in a high success rate for pit and fissure sealant or preventive resin restorations.

Example 3

Partial or Complete Removal of Composite Restorations and Repair at Failure Sites

| Operating Conditions: | |
|---|---|
| Particle Energy | 60 psi |
| Abrasive Powder | Aluminum Oxide 27.5 micron GammaPure ™ |
| Beam Intensity | 3–5 grams/minute |
| Mode | MicroPulse ™ |
| Nozzle Diameter | 0.014–0.018 inch Standard or SST |

-continued

| Operating Conditions: | |
|---|---|
| Time | As required to obtain desired result |

Procedure: The air abrasion unit of this invention removes composite material very efficiently and quite rapidly. The composite materials are removed at a faster rate than enamel or dentin. The nozzle is directed at the area to be prepared and proceeds with series of short, incremental cuts. The repair process is continued with traditional etching and restorative methods.

During the partial removal and repair of a composite restoration, providing an undercut in the preparation may be desirable. To avoid etching adjacent teeth, a strip of rubber dam is used to prevent overspray.

Example 4

Using the Air Abrasion Unit of this Invention to Etch, Metal, Porcelain, or Composite Restorations Prior to Repair

| Operating Conditions: | |
|---|---|
| Particle Energy | 60 psi |
| Abrasive Powder | Aluminum Oxide 27.5 micron GammaPure ™ |
| Beam Intensity | 4–5 grams/minute |
| Mode | Continuous |
| Nozzle Diameter | 0.014–0.018 inch Standard |
| Time | 5–20 seconds/site as required |

Procedure: The air abrasion unit of this invention is indicated to roughen and provide a satin finish to metal, porcelain, and composite restorations prior to etching and repairing them. The nozzle, as specified above, is directed at the surface to be repaired at a distance of 5–6 mm. It is moved in a sweeping motion to frost the surface. Care is taken not to keep the nozzle in one area as undesirable cutting may occur. The unit may be used to clean, remove oxidation, stain, and plaque, and prepare surfaces prior to acid etching.

The air abrasive unit of this invention may be used to prepare amalgam or stainless steel restorations prior to overlaying with a composite material for cosmetic purposes. The procedure is not intended to replace acid etching for bonding.

Example 5

Using the Air Abrasion Unit of this Invention to Remove Stains and Calculus from Enamel, Dentin, and Cementum

| Operating Conditions: | |
|---|---|
| Particle Energy | 20–40 psi |
| Abrasive Powder | 27.5 micron Aluminum Oxide, Dolomite or Sodium Bicarbonate |
| Beam Intensity | 2–3 grams/minute |
| Mode | Continuous |
| Nozzle Diameter | 0.018 inch Standard |
| Time | As required |

Procedure: At a distance of 5–10 millimeters in a continuous sweeping motion, the nozzle was directed at the material, such as stains or calculus, to be removed from the tooth surface. If aluminum oxide is used, it is possible to cut tooth structure, so care must be taken if it is used for cleaning purposes. Tooth structure may be removed by aluminum oxide even when small nozzles and low air pressures are used. The aluminum oxide will also leave a frosted surface that must be polished.

If sodium bicarbonate or dolomite are used, stain, plaque, or calculus will be removed without removing tooth structure. Sodium bicarbonate or dolomite will also polish tooth surfaces.

This procedure is useful during restorative procedures to debride tooth surfaces using 27.5 micron aluminum oxide. For strictly prophylactic procedures, the use of dolomite or sodium bicarbonate is recommended.

Example 6

Removal of Spent Amalgam with the Air Abrasion Unit of this Invention

| Operating Conditions: | |
|---|---|
| Particle Energy | 80 psi |
| Abrasive Powder | 27.5 micron Aluminum Oxide |
| Beam Intensity | 8–10 grams/minute |
| Mode | PowerPulse ™ |
| Nozzle Diameter | 0.018 inch SST |
| Time | May require 2–3 minutes for complete removal of small amalgam restorations |

Procedure: With the nozzle at a constant cutting distance of 1–5 mm, short, incremental cuts are made with the nozzle directed at the material to be removed. This is continued until removal is complete, including any decay that may be present. The procedure is continued with traditional etching and restorative methods.

The procedure is not efficient at removing large or deep Class II amalgam restorations, nor is it indicated to replace acid etching for bonding. It is possible to debulk amalgam restorations with a traditional high speed handpiece and 330 carbide bur, and then switch to air abrasion methods to finish removal of amalgam and cavity preparation.

High volume evacuation (HVE) is provided with standard high volume evacuation such as the Kreativ KleanAir® II, set on high speed at a distance about 8 inches from the patient's chin.

GENERAL DISCUSSION

The dental instrument 1 features a microprocessor controlled pulsed stream. This pulsed stream allows for greater control of the air abrasive process by the dentist. The instrument 1 provides greater control over the pulsed stream, the flow of abrasive material, and air mixture through the nozzle 116a. The desired control over the process is a result of the pulsed or continuous flow mechanisms as directed by the central microprocessor 110. In this invention, the central microprocessor 110 allows control of abrasive loading, the pulse duration and pressure to optimize impact velocity of the abrasive material to the degree desired by the dentist.

The dental instrument 1 may be used to remove unwanted dental material, such as decay, debris, carious enamel, carious dentin, cementum, spent amalgam, stains, calculus, materia alba, organic plug, composites, resin restoratives, and the like. The present invention uses impingement of fine, abrasive particles entrained in a high velocity air stream to remove such materials. The abrasion process enabled by the dental instrument 1 is inherently free from vibration problems because the instrument is not in contact with the tooth.

The abrasive materials that may be used in the process of this invention include sodium bicarbonate, urea, dolomite, aluminum oxide, or the like. An often used abrasive material is aluminum oxide. Aluminum oxide, or alumina, used for dental air abrasion may be in particle size ranging from about 27 to about 50 microns in size. A preferred size of aluminum oxide is 27.5 microns and is available from Kreativ, Inc. as GammaPure™, U.S. patent application Ser. No. 08/873,526, filed Jun. 12, 1997, and entitled Abrasive Dental Composition and Method for Use. The abrasive material flow ranges from about 1 to about 5 grams per minute.

The mechanism of material removal by an abrasive air stream may be considered a process of brittle material failure. The failure of brittle substances, such as decayed dental material, occurs by a process of crack creation, extension, and erosion. When the abrasive particles impact such a surface, the depression grows, and radial and lateral cracks are generated in this area. These cracks ultimately join together to isolate and remove an area of decayed material. Controlled pulsing of the delivery of the abrasive to the tooth surface maximizes the efficiency of the process. More specifically, optimization of the flow path of the abrasive particles is achieved by a microprocessor-controlled pulse. This delivery means transfers the optimal amount of energy from the abrasive particle to the target tooth surface. As the instrument 1 is used by a dentist, the central microprocessor 110 can quickly and dynamically adjust all parameters according to the dentist's specific needs and desires.

In an article in FOCUS, Rosenberg states that air abrasive dental units cut faster when pulsed. Automatic pulsing offers a high-efficiency cutting mode that allows rapid removal of tooth structure at lower air pressure. Optimal timing of these pulses is critical to maximizing cutting efficiency. If the pulses are too far apart, each pulse will dissipate into the energy of continuous flow before the next pulse occurs. If the pulses are too close together, they function as a continuous stream.

An earlier dental air abrasion system used was the Mach 4.1™, offered by Kreativ, Inc. This unit allowed the choice of two cutting modes. The choices were either continuous or pulsed, where the pulse speed and frequency were pre-set. The unit enabled rapid removal of unwanted tooth structure using pressures as low as 45 psi. This unit was not equipped with a microprocessor and did not allow the pulse rates to be varied as provided by the instrument 1. Other available air abrasion units either do not pulse at all or have controlled, automatic, pre-set pulsing that may be selected but cannot be controlled by the user. For example, abrasive powder flow rates may be chosen from low, medium, and high selections. This type of unit utilizes a circuit board and solid-state relay logic.

There are several improvements from these earlier air abrasion units made possible through microprocessor control. First, self-diagnostics of the pinch valves 104A and 104B and of the powder level in the canister 109b. Second, conversion to electronic control from manual control. This improvement greatly facilitates fine-tuning the instrument by the user. These adjustments in operating conditions may be easily made by the dentist while working on a patient by pressing up/down buttons 202, 203, 204, and 205. Increased control aids in preventing desirable tooth structure from being accidentally abraded. Increased control of the abrasive flow provides less indiscriminate contact between the spent abrasive and other areas in the mouth, which can cause unwanted untidiness and require additional clean-up. Further reasons for the desired variety and control of abrasive flow include improved control over the cutting process, better cutting efficiencies, the ability to function at lower, safer air pressures and the like. The central microprocessor 110 is capable of start-up self testing as well as dynamic adjustments during the cutting process. These parameters include powder levels in the canister 109b, pinch valve/tube monitoring, air pressure regulation, monitoring the operator input air pressure, automatic recognition and monitoring of line frequencies, monitoring power supplies, and automatic shutdown if pressure gets too high.

Using the instrument 1, cutting speed increases with increasing air pressure, increased powder flow, and decreased distance to the tooth structure. Since enamel cuts slower than dentin, it may take one or two minutes to complete a Class I preparation on a molar. Similarly, it may only take 5 seconds to complete a Class V preparation on a premolar. Increased powder flow and air pressure will increase cutting speed, and will deliver more powder to the operative site that preferably is controlled with the high volume evacuation device. Most procedures may be accomplished with about 20–120 psi pressure and a powder flow of about 2–5 grams/minute powder flow.

The instrument 1 has three selectable parameters: Power Pulse™, Micro Pulse™, and continuous modes. The dentist may choose the desired mode. The Power Pulse™ setting is selected and used for the removal of amalgam with the use of the supersonic nozzle 116a. This setting is adjusted for maximum cutting efficiency. When this mode is selected, the program adjusts the ON/OFF pulse timing for optimized abrasive/air flow. The PowerPulse™ mode also automates incremental cutting. The pulse rate is specifically designed to provide optimum cutting efficiency for amalgam removal. The Power Pulse setting is adjusted for maximum cutting efficiency while using the supersonic nozzle 116a. When this mode is selected, the central microprocessor 110 adjusts the ON/OFF pulse durations for the abrasive air flow. A preferred ON time for the abrasive pinch valve in this mode may range from about 190 to about 250 milliseconds. Similarly, the preferred OFF time may range from about 80 to about 140 milliseconds. The central microprocessor 110 may be replaced with a microprocessor reprogrammed to customize these ON/OFF times to fit the individual needs of dentists.

The Micro Pulse™ mode automates incremental cutting and the pulse rate provides optimum cutting efficiency of tooth structure. When the Micro Pulse™ mode is selected, the dentist desires high efficiency cutting for precise removal of tooth structure using a standard (non-supersonic) handpiece and nozzle. When the MicroPulse™ setting is selected, the program adjusts the ON/OFF pulse timing for the abrasive/air flow. An optimal range of ON time for this mode is from about 235 to 295 milliseconds. Similarly, the OFF times may range from about 30 to about 80 milliseconds using the standard handpiece. Again, The central microprocessor 110 may be replaced with a microprocessor reprogrammed to customize these ON/OFF times to fit the individual needs of dentists.

The continuous mode is selected for less aggressive air abrasion applications. This setting does not pulse the abrasive stream at all. When this mode is selected, the footswitch allows the abrasive pinch valve 104A to remain open and let the powder flow continuously. The velocity of the particles are less than in pulse mode. This allows the practitioner a wider range of powder flow selection.

It is desirable to use standard high volume evacuation (HVE) to insure patient comfort and successful air abrasion dental procedures. This HVE system is standard equipment in all dental operatories. It should be placed in close proximity to the operative site. Additional external equipment is also recommended. The additional HVE should be used to catch the deflecting stream of air and particles so they do not impinge on soft tissue. A preferred HVE system is the KleanAir II™ Filtration System, from Kreativ, Inc.

The main central microprocessor 110 uses as the sensor 10 a calibrated pressure transducer that gives the processor pressure readings for monitoring air pressure fluctuations. The main central microprocessor 110 also monitors if the handpiece safety switch 117 has been toggled. If the handpiece 116 is in the cradle 115, the switch 117 is closed. The foot switch 121 will be ignored until the handpiece 116 is removed. When the handpiece is removed from the cradle 115, the switch 117 is toggled to the open position, and the foot switch 121 becomes activated.

To begin powder flow, air pressure must be present, the safety switch 117 toggled, and the foot pedal 68 depressed. The central microprocessor 110 will start vibrating the vibrator 62 and will start sequencing the pinch valves 104a through 104C. If there is powder in the powder chamber 52, the powder will start to flow according to the operating parameters set. If there is no powder in the unit, only air will flow. Once flow has started, no further adjustments using the remote control unit 118 can be made until the foot pedal 68 is released.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

We claim:

1. An air abrasion dental instrument including
    a handpiece having a nozzle from which is ejected a stream of abrasive particles
    a valve operated under the control of a microprocessor which regulates, as selected by a user, the stream of abrasive particles either as a continuous flowing stream or a pulsed flowing stream, and
    a remote control unit small enough to fit into the palm of a hand of a user which signals the microprocessor to provide control of the stream.

2. The dental instrument of claim 1 where the microprocessor enables the valve to be operated at a plurality of different pulse durations.

3. The dental instrument of claim 2 where the handpiece has a supersonic nozzle and the pulse duration as adjusted by the microprocessor has an ON time ranging from 190 to 250 milliseconds and an OFF time ranging from 80 to 140 milliseconds, whereby amalgam removal is facilitated.

4. The dental instrument of claim 2 where the pulse duration as adjusted by the microprocessor has an ON time ranging from 235 to 295 milliseconds and an OFF time ranging from 30 to 80 milliseconds, whereby precision control for cavity preparation is facilitated.

5. The dental instrument of claim 1 where in the continuous flowing stream the pressure ranges from 20 to 40 psi, and the abrasive particle flow rate is from 2 to 3 grams per minute, whereby cleaning, stain removal, and small lesion treatment is facilitated.

6. The dental instrument of claim 1 where the handpiece has a Z axis and the stream is sent through the nozzle held in an assembly at an angle ranging from 45° to 90° with respect to the Z axis.

7. The dental instrument of claim 1 where the nozzle has a diameter ranging between 0.01 and 0.03 inch.

8. The dental instrument of claim 1 where the handpiece is integrated with a main dental unit foot control for a dental drill, so that said main dental unit foot control selectively operates both the dental drill and the handpiece.

9. The dental instrument of claim 1 where, when not in use, the handpiece is seated in a cradle on the remote unit having a safety switch which is engaged by the handpiece when seated in the cradle to enable the microprocessor to recognize when a user is holding the handpiece.

10. The dental instrument of claim 1 including a collection canister into which abrasive particles in the handpiece are collected when the flow of the stream is discontinued.

11. The dental instrument of claim 1 including an air supply system having an on-off valve which is opened and closed rapidly to bring the instrument to a selected pressure.

12. The dental instrument of claim 1 where the stream has a plurality of operating parameters, and the instrument includes a non-volatile read/write memory which retains the last selected values of the parameters of the stream of abrasive particles.

13. The dental instrument of claim 1 in which the microprocessor is programmed to provide a self-diagnostic routine.

14. The dental instrument of claim 1 in which the microprocessor is programmed to hold particle flow the instrument at a standby condition until a user manually actuates the instrument.

15. An air abrasion dental instrument including
a handpiece having a nozzle from which is ejected a stream of abrasive particles,
a valve operated under the control of a microprocessor which regulates, as selected by a user, the stream of abrasive particles either as a continuous flowing stream or a pulsed flowing stream, and
a warning system having audio indicators which alert the user that a defective condition prevails.

16. The dental instrument of claim 15 where the defective condition is a defective valve, the instrument needs service, an inadequate supply of abrasive powder, an inadequate available pressure, a leaking fluid supply line or an inability to reach or sustain desired voltages for the instrument's operation.

17. The dental instrument of claim 15 where the microprocessor enables the valve to be operated at a variety of different pulse durations.

18. An air abrasion dental instrument including
a handpiece having a nozzle from which is ejected a stream of abrasive particles,
a valve operated under the control of a microprocessor which regulates, as selected by a user, the stream of abrasive particles either as a continuous flowing stream or a pulsed flowing stream, and
an audio alarm which is activated when a defective condition prevails.

19. The dental instrument of claim 18 where the defective condition is that an air pressure selected by the user exceeds a limit of the instrument, an abrasive loading selected by the user by the user exceeds a limit of the instrument, a safety switch for the handpiece for the instrument indicates that the handpiece has not been lifted from a cradle for the handpiece.

20. A system which delivers to a plurality of different operatories, under the control of a user in each individual operatory, separate streams of abrasive particles, said system including
in each individual operatory a handpiece from which is ejected a stream of abrasive particles,
each handpiece having a first operational mode that provides a pulsed stream of particle laden gas and a second operational mode that provides a continuous stream of particle laden gas,
each operatory being under the common control of a microprocessor which allows the user at each individual operatory to select the operational mode of the handpiece at such individual operatory, and
a remote control unit small enough to fit into the palm of a hand of a user which signals the microprocessor to provide control of the stream.

21. An air abrasion dental instrument, including
a handpiece from which a stream of particle laden gas is ejected,
a mixing chamber in which abrasive particulates are mixed with gas flowing through said mixing chamber,
a first valve which has an open (or on) position and a closed (or off) position, said first valve in the open (or on) position permitting gas to flow into the mixing chamber and in the closed (or off) position preventing gas to flow into the mixing chamber, to enable gas pressure within said mixing chamber to be increased incrementally,
a second valve between the mixing chamber and the handpiece, said second valve being operated at a first operational mode that provides a pulsed stream of particle laden gas or at a second operational mode that provides a continuous stream of particle laden gas,
a pressure sensor which detects the pressure of the gas within the mixing chamber and provides a control signal indicating the pressure detected,
a remote control unit which is small enough to fit into the palm of a hand of a user that enables a user to select (a) the pressure of the gas within the mixing chamber and (b) the operational mode, and
a microprocessor which controls the operation of the first valve to turn said first valve between open and closed positions until the gas pressure of said stream corresponds to the gas pressure selected by the user actuating the remote control unit.

22. The dental instrument of claim 21 where the remote control unit also enables a user to select the concentration of particles in the gas steam.

23. The dental instrument of claim 21 where the pressure of the mixing chamber is increased incrementally by selectively opening and closing the first valve.

24. The dental instrument of claim 21 where the first operational mode is achieved by selectively opening and closing the second valve to create the pulsed stream and the second operational mode is achieved by maintaining the second valve continuously open to create the continuous stream.

25. The dental instrument of claim 21 where pulsed stream of the first operational mode is at different pulse durations as selected by a user.

26. The dental instrument of claim 21 where the handpiece is operated under the control of a foot control.

27. An air abrasion dental instrument including a handpiece having a nozzle from which is ejected a stream of abrasive particles, said stream having a plurality of operating parameters, a valve operated under the control of a microprocessor which controls the flow of the stream of abrasive particles, and a remote control unit that is small enough to fit into the palm of a hand of a user that is operated manually by a user which signals the microprocessor to adjust the parameters for the stream as selected by the user.

28. The dental instrument of claim 27 where the stream of abrasive particles is either a continuous flowing stream or a pulsed flowing stream, and the microprocessor enables the valve to be operated at a plurality of different pulse durations.

29. The dental instrument of claim 27 where the handpiece is integrated with a main dental unit foot control for a dental drill, so that said main dental unit foot control operates both the dental drill and the handpiece.

30. The dental instrument of claim 27 where, when not in use, the handpiece is seated in a cradle on the remote unit having a safety switch which is engaged by the handpiece when seated in the cradle to enable the microprocessor to recognize when a user is holding the handpiece.

31. An air abrasion dental instrument including a handpiece having a nozzle from which is ejected a stream of abrasive particles, a sensor which detects the pressure of the stream of abrasive particles, an air supply system having an on-off valve which is opened and closed rapidly to bring the stream of abrasive particles to a selected pressure, a microprocessor which controls the operation of the on-off valve in response to the pressure detected by the sensor to regulate the pressure of the stream of abrasive particles, and a remote control unit small enough to fit into the palm of a hand of a user operated manually by a user, said remote control unit signaling the microprocessor to set the pressure of the stream of abrasive particles to a pressure selected by the user.

32. The dental instrument of claim 31 including a non-volatile read/write memory which retains the last selected pressure.

33. The dental instrument of claim 31 including an audio alarm which is activated when one or more of the following conditions prevail: an air pressure selected by the user exceeds the limits of the instrument, an abrasive loading selected by the user exceeds the limits of the instrument, a safety switch for the handpiece for the instrument indicates that the handpiece has not been lifted from a cradle for the handpiece.

34. An air abrasion dental instrument including a handpiece having a nozzle from which is ejected a stream of abrasive particles, said stream having a plurality of operating parameters, a valve operated under the control of a microprocessor which controls the flow of the stream of abrasive particles, and a remote control unit small enough to fit into the palm of a hand of a user that is operated manually by a user which signals the microprocessor to adjust the parameters of the stream, said handpiece being integrated with a main dental unit foot control for a dental drill, so that said main dental unit foot control operates both the dental drill and the handpiece.

35. An air abrasion dental process wherein a stream of abrasive particles is directed at a tooth structure, said stream being created by opening and closing a valve operated by a microprocessor which responds to command signals from a remote control unit small enough to fit into the palm of a hand of a user that includes a selector control which enables a user to select either a pulsed stream or a continuous stream.

36. The process of claim 35 where said abrasive particles are at a relatively high particle speed ranging from 110 to 160 meters per second and at an abrasive particle flow rate ranging from 1 to 10 grams per minute, and said stream is at a pressure ranging from 20 to 120 psi.

37. The process of claim 35 used to remove amalgam from the tooth structure, where said stream is directed at the tooth structure through a supersonic nozzle with said stream being in the form of pulses and the pressure of the stream exceeding 40 psi and the abrasive particle flow rate ranging from 1 to 10 grams per minute.

38. The process of claim 35 where the handpiece has a Z axis and the handpiece nozzle is held in an assembly at an angle ranging from 45° to 90° with respect to the Z axis and has a diameter of from 0.01 inch to 0.03 inch.

39. The process of claim 35 used to prepare a tooth structure for veneer restoration, facing restoration, pit and fissure sealants, partial or complete removal of composite restorations, or repair of restoration failure sites where said stream is directed as a pulsed stream at the tooth structure at a pressure of from 40 to 80 psi and the abrasive particle flow rate is up to 5 grams per minute.

40. The process of claim 39 where the handpiece has a Z axis and the the nozzle is held in an assembly at an angle ranging from 45° to 90° with respect to the Z axis and has a diameter of from 0.01 inch to 0.03 inch.

41. The process of claim 39 where the nozzle is a supersonic nozzle.

42. The process of claim 35 used to prepare a tooth structure for etching metal, porcelain, or composite restorations prior to repair, where said stream is directed at the tooth structure as a continuous, non-pulsed stream at a pressure of less than 80 psi and the abrasive particle flow rate is up to 5 grams per minute.

43. The process of claim 35 used to clean a tooth structure where said stream is directed at the tooth structure as a continuous, non-pulsed stream at a pressure of from 20 to 40 psi and the abrasive particle flow rate ranges from about 2 to 3 grams per minute.

44. The process of claim 43 where the nozzle has a diameter of substantially 0.018 inch.

45. The process of claim 35 where the abrasive particles are selected from the group consisting of aluminum oxide, dolomite, and sodium bicarbonate.

46. The process of claim 35 where pulse duration of the stream is manually selected through the remote control unit.

47. An air abrasion dental instrument including a handpiece having a nozzle from which is ejected a stream of abrasive particles, a valve operated under the control of a microprocessor which regulates, as selected by a user, the stream of abrasive particles either as a continuous flowing stream, or a pulsed flowing stream and an air supply system having an on-off valve which is opened and closed rapidly to bring the instrument to a operating pressure selected by a user.

48. An air abrasion dental instrument which provides a stream of abrasive particles at pressures ranging from 15 to 120 psi with an abrasive loading ranging from 1 to 10 grams/minute as selected by the user through a control system including a microprocessor with a remote control unit small enough to fit into the palm of the hand of a user that provides fingertip control of the instrument's pressure and abrasive loading of the stream without having to move away from the patient.

* * * * *